US012806020B2

(12) United States Patent
Goldsmith

(10) Patent No.: US 12,806,020 B2
(45) Date of Patent: Nov. 24, 2026

(54) VASCULAR VALVES AND SERVOVALVES—AND SIMPLIFIED VASCULAR BYPASS HEART TRANSPLANTATION

(71) Applicant: David S. Goldsmith, Atlanta, GA (US)

(72) Inventor: David S. Goldsmith, Atlanta, GA (US)

( * ) Notice: Subject to any disclaimer, the term of this patent is extended or adjusted under 35 U.S.C. 154(b) by 0 days.

(21) Appl. No.: 19/301,399

(22) Filed: Aug. 15, 2025

(65) Prior Publication Data

US 2025/0366992 A1 Dec. 4, 2025

Related U.S. Application Data

(63) Continuation-in-part of application No. 19/033,348, filed on Jan. 21, 2025, which is a continuation-in-part of application No. 16/873,914, filed on Aug. 11, 2020, now abandoned.

(51) Int. Cl.
*A61F 2/24* (2006.01)
*A61L 27/18* (2006.01)

(52) U.S. Cl.
CPC ............ *A61F 2/2476* (2020.05); *A61L 27/18* (2013.01); *A61F 2210/0057* (2013.01); *A61F 2250/0082* (2013.01); *A61L 2430/20* (2013.01)

(58) Field of Classification Search
CPC ........... A61F 2/2476; A61F 2250/0082; A61B 2017/00243; A61B 2017/00969; A61B 2017/1107; A61B 2017/1135; A61M 2210/12; A61M 2039/0258; A61M 2039/0261; A61M 2039/027; A61M 2039/0276; A61M 60/161; A61M 1/3655; A61M 27/002
See application file for complete search history.

(56) References Cited

U.S. PATENT DOCUMENTS

| | | | |
|---|---|---|---|
| 5,458,615 | A | 10/1995 | Klemm et al. |
| 5,509,888 | A | 4/1996 | Miller |
| 5,534,007 | A | 7/1996 | St. Germain et al. |
| 5,772,669 | A | 6/1998 | Vrba |
| 5,792,144 | A | 8/1998 | Fischell et al. |
| 5,891,154 | A | 4/1999 | Loeffler |

(Continued)

*Primary Examiner* — Kevin C Sirmons
*Assistant Examiner* — William R Frehe
(74) *Attorney, Agent, or Firm* — Meunier Carlin & Curfman LLC

(57) ABSTRACT

A perivascular valve device includes a valve body and define an integral tubular blood outlet passageway sidestem extending perpendicularly from said valve body, the outlet passageway being continuous with a lumen of the blood vessel, wherein the perivascular valve is selectively positional, such that the perivascular valve with sidestem can be positioned at any anatomically available level and rotational angle along the blood vessel. The outlet passageway can have a driven polymeric tongue having an upturned front end configured as a blood outflow diversion chute which is extendable a controllable distance into the lumen of the blood vessel so as to draw off a controllable volume of blood between zero and one hundred percent into said passageway for discharge through the outlet passageway sidestem. The valve body comprises a stretchable material comprising expandable furrows to allow radial expansion of the perivascular valve so as to accommodate growth in pediatric patients.

8 Claims, 4 Drawing Sheets

(56) References Cited

U.S. PATENT DOCUMENTS

| | | | |
|---|---|---|---|
| 5,910,145 | A | 6/1999 | Fischell et al. |
| 5,951,585 | A | 9/1999 | Cathcart et al. |
| 5,980,533 | A | 11/1999 | Holman |
| 6,190,353 | B1 | 2/2001 | Makower et al. |
| 6,200,325 | B1 | 3/2001 | Durcan et al. |
| 6,342,066 | B1 | 1/2002 | Toro et al. |
| 6,379,365 | B1 | 4/2002 | Diaz |
| 6,380,457 | B1 | 4/2002 | Yurek et al. |
| 6,613,075 | B1 | 9/2003 | Healy et al. |
| 6,695,812 | B2 | 2/2004 | Estrada et al. |
| 6,743,243 | B1 | 6/2004 | Roy et al. |
| 6,755,855 | B2 | 6/2004 | Yurek et al. |
| 6,932,091 | B2 | 8/2005 | Frazier et al. |
| 7,641,668 | B2 | 1/2010 | Perry et al. |
| 7,983,766 | B1 * | 7/2011 | Thacker ............... A61N 1/0558 607/117 |
| 8,224,449 | B2 | 7/2012 | Carbunaru et al. |
| 8,518,062 | B2 | 8/2013 | Cole et al. |
| 9,192,706 | B2 | 11/2015 | Bulent et al. |
| 11,759,186 | B2 | 9/2023 | Goldsmith |
| 2001/0044631 | A1 | 11/2001 | Akin et al. |
| 2002/0072758 | A1 | 6/2002 | Reo et al. |
| 2006/0282106 | A1 | 12/2006 | Cole et al. |
| 2007/0038259 | A1 | 2/2007 | Kieval et al. |
| 2008/0161865 | A1 | 7/2008 | Hagen |
| 2010/0076247 | A1 | 3/2010 | Zilbershlag et al. |
| 2010/0121438 | A1 | 5/2010 | Jarvik |
| 2011/0213309 | A1 | 9/2011 | Young et al. |
| 2011/0264116 | A1 | 10/2011 | Kocur et al. |
| 2015/0190561 | A1 | 7/2015 | Bulent et al. |
| 2016/0000985 | A1 | 1/2016 | Consigny et al. |
| 2016/0051806 | A1 * | 2/2016 | Goldsmith ............... A61N 1/00 604/21 |
| 2016/0144165 | A1 * | 5/2016 | Young .................. A61N 1/0534 607/116 |
| 2016/0199065 | A1 | 7/2016 | Consigny et al. |
| 2017/0165458 | A1 | 6/2017 | Yu |
| 2018/0085513 | A1 * | 3/2018 | Cull .................... A61M 39/227 |
| 2019/0374213 | A1 | 12/2019 | Goldsmith |

* cited by examiner

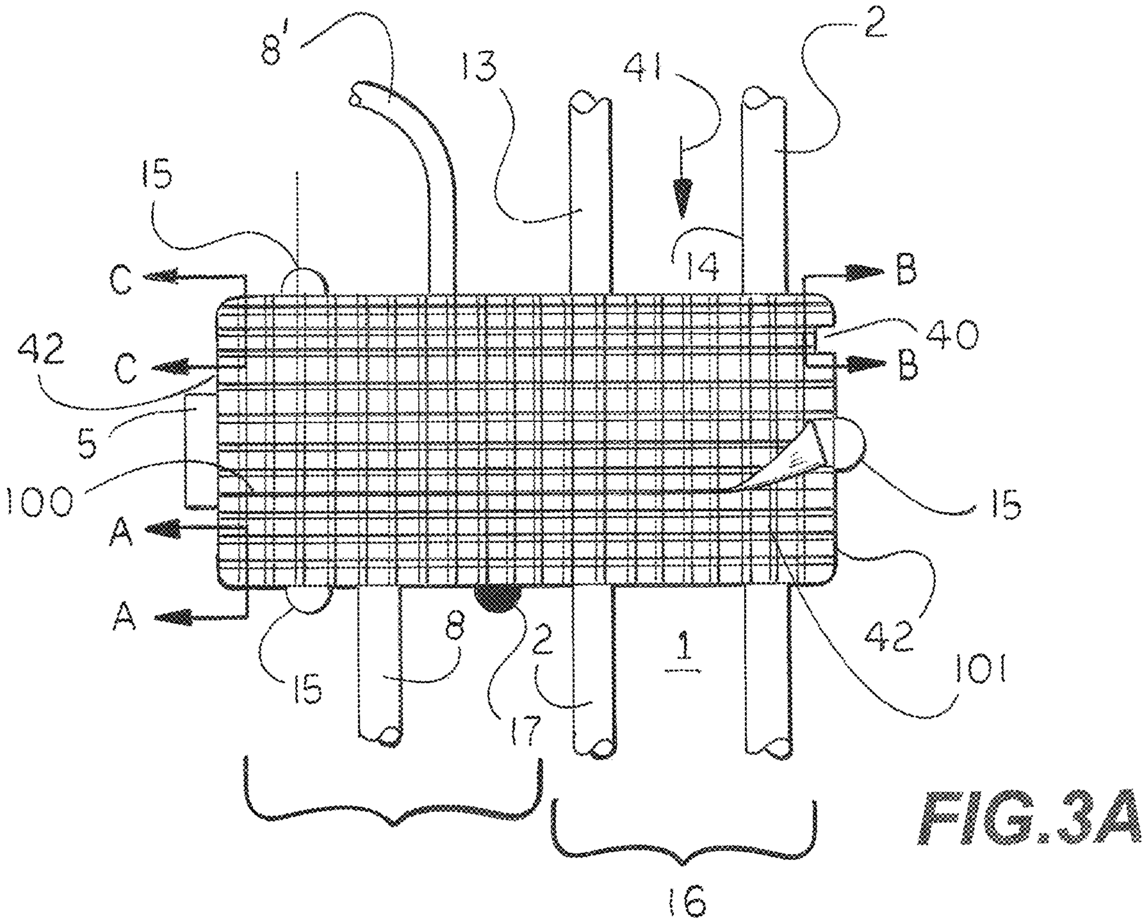
FIG.3A
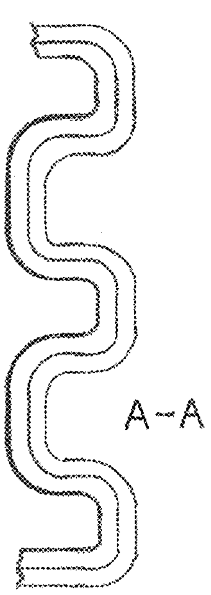
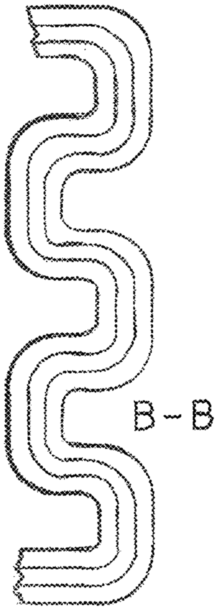
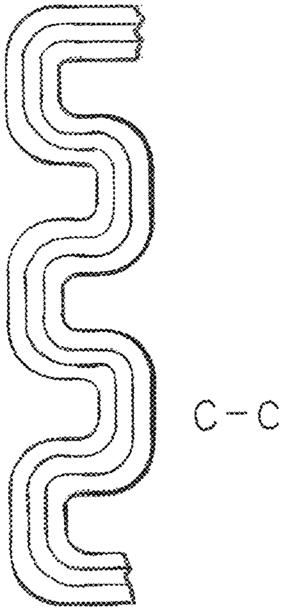
FIG.3B FIG.3C FIG.3D

VASCULAR VALVES AND SERVOVALVES—AND SIMPLIFIED VASCULAR BYPASS HEART TRANSPLANTATION

CROSS REFERENCE TO RELATED APPLICATIONS

This application is a continuation-in-part of U.S. patent application Ser. No. 19/033,348, filed Jan. 21, 2025, entitled, "VASCULAR VALVES AND SERVOVALVES—AND PROSTHETIC DISORDER RESPONSE SYSTEMS", which claims priority to U.S. patent application Ser. No. 16/873,914, filed Aug. 11, 2020, entitled, "VASCULAR VALVES AND SERVOVALVES—AND PROSTHETIC DISORDER RESPONSE SYSTEMS", which claims the benefit of U.S. Provisional Application No. 69/922,526, filed on Aug. 13, 2019, the contents of which are herein incorporated by reference in their entirety for all purposes.

FIELD OF THE INVENTION

Provided are vascular valves for use by pediatric cardiac and general surgeons to perform heart transplants on patients born with a heart so malformed that no currently conventional method of repair could initiate the normal pulsatile circulation essential for unimpaired physical and mental development. The valves provided herein are also suitable for use in any other solid organ or gland of a child, such as in a urological, hepatological, or pulmonary contexts.

BACKGROUND

The earlier in life a severely if not unsurvivably malformed heart or other organ can be replaced, the less will be the maldevelopment that would ensue were the native organ repaired using conventional surgery. The same applies to deficits in hormones or enzymes due to defective or missing glands. Often demanding three operations that result in long-term postoperative pain, the surgery is unable to initiate the normal pulsatile blood flow essential for normal development. Moreover, largely owing to the surgical trauma wrought, the alternative approach to effecting recovery, a conventional pediatric heart transplant, yields inadequate durability of the graft organ which will necessitate reimplantation at a time still early in life, almost certainly to be followed by at least one if not more reimplantations.

The elimination of much trauma is critical in rendering children otherwise judged incapable of tolerating the conventional procedure to undergo an organ transplant that averts the secondary maldevelopment associated with a defective organ. Aside from the inadequate pool of replacement organs to support multiple reimplantations for a single patient, to undergo such treatment foreshadows a life of illness, pain, and apprehension. To overcome this eventuality, a means for organ transplantation which eliminates much of the trauma that causes the graft organ to deteriorate combined with means for implementing a surgical method for organ transplantation and follow-up treatment so that no more than one reimplantation is required from infancy to adulthood, is needed.

Because replacement of the defective heart occurs early in life, ideally in early infancy, solutions must be able to accommodate exceptionally rapid growth.

SUMMARY

In some aspects, the systems and methods described herein relate to a perivascular valve device for encircling a blood vessel of a pediatric patient. The perivascular device can include a valve body and define an integral tubular blood outlet passageway sidestem extending perpendicularly from said valve body, the outlet passageway being continuous with a lumen of the blood vessel, wherein the perivascular valve is selectively positional, such that the perivascular valve with sidestem can be positioned at any anatomically available level and rotational angle along the blood vessel. The outlet passageway can have a driven polymeric tongue having an upturned front end configured as a blood outflow diversion chute which is extendable a controllable distance into the lumen of the blood vessel so as to draw off a controllable volume of blood between zero and one hundred percent into said passageway for discharge through the outlet passageway sidestem. The valve body comprises a stretchable material comprising expandable furrows to allow radial expansion of the perivascular valve so as to accommodate growth in the pediatric patient.

In some implementations, the stretchable material is made of a chemically inert and elastic polymer. In some implementations, the polymer is silicone rubber. In some implementations, stretchable material is made of a plasticized and chemically inert polymer. In some implementations, the polymer is polyetheretherketone.

In some implementations, the tongue has a feathered surround area which extends radially outward as the valve enlarges so as to remain flush against anterior and lateral interior walls of the blood vessel throughout growth of the pediatric patient. In some implementations, the tongue is driven in extension and retraction under continuously variable control by a servomotor that is operatively connected to the perivascular valve. In some implementations, the tongue is directly driven in extension and retraction between zero and one hundred percent discharge as controlled by a plunger solenoid.

In another aspect, the systems and methods described herein relate to a perivascular valve system for encircling a blood vessel of a pediatric patient. The perivascular valve system can include a perivascular valve configured to be selectively positionable along and about a tubular anatomical structure and an outer covering layer. The outer covering layer can include two stretchable semicylindrical halves pivotably joined together along a common edge such that, when opened and placed to encircle the tubular anatomical structure, the two stretchable semicylindrical halves grip about the tubular anatomical structure, thereby forming a stationary collar. The perivascular valve is continuous with a lumen of the tubular anatomical structure, thereby facilitating delivery of drugs and cabled devices into the lumen of the tubular anatomical structure, and wherein the perivascular valve further include a tongue configured to enter the lumen of the tubular anatomical structure and divert a measured portion of bodily fluid passing therethrough. In some implementations, the perivascular valve system can further include a cushioning layer of viscoelastic polyurethane foam bonded to the underside of the outer covering layer to protect small nerves and vessels that enter and depart from a adventitia of the tubular anatomical structure, and wherein the perivascular valve defines perforations passing entirely through the outer covering layer and the cushioning layer to expose the adventitia, wherein, when the perivascular valve expands radially, the outer covering layer and the cushioning layer expand radially in unison such that diameters of that the perforations expand in unison, wherein diameters of the perforations within the outer covering layer remain equal to diameters of the perforations within the cushioning layer as the perivascular valve expands radially, and wherein neither the outer covering layer nor the cushioning layer restrains expansion of the other.

BRIEF DESCRIPTION OF THE FIGURES

FIG. 3 shows a vascular valve for use in a vascular bypass solid organ transplant on a small child where the valve, to be left implanted on completion of the operation, the degree and rate of growth to ensue must be accommodated to extend to late adolescence if not adulthood, and so doing, exceed that estimable of the ordinary vascular valve described in copending continuation-in-part application Ser. No. 19/033,348 shown in the preceding drawing figure.

DETAILED DESCRIPTION

Figure 1:
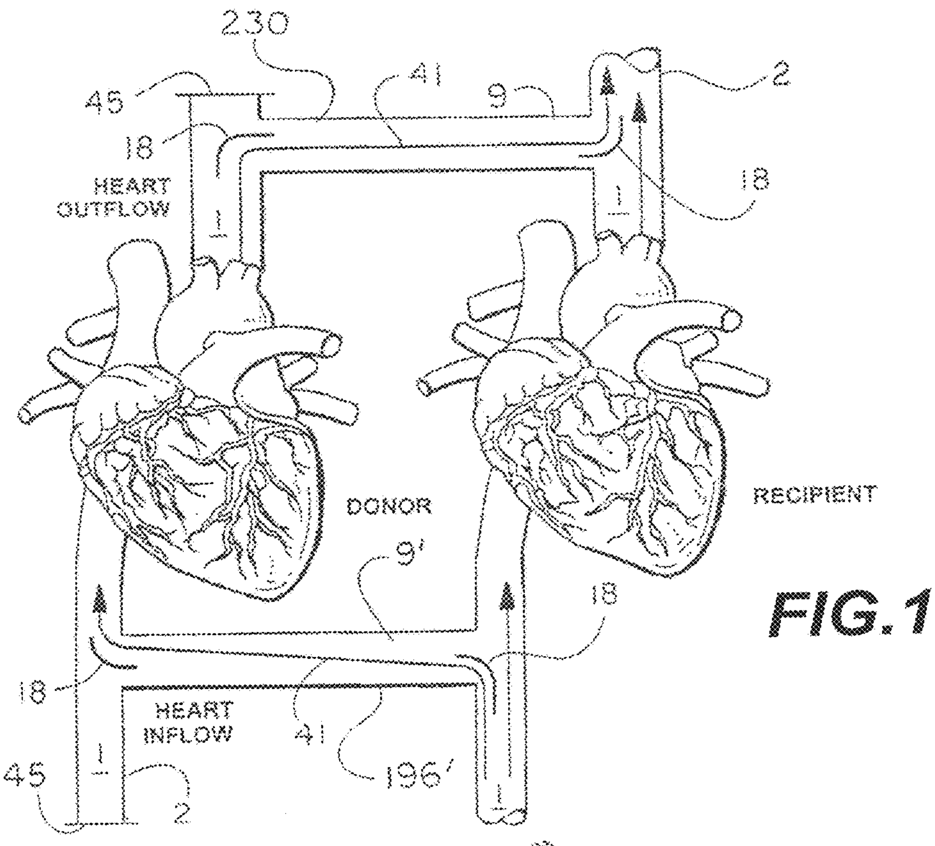
FIG. 1 shows the blood flow pattern at the midway point in transferring a graft heart from the circulatory system of the donor into that of the recipient. The connections between the hearts are shown in the abstract without showing the detailed valving on each of the pertinent great vessels, which understood by cardiac surgeons, would require many drawing figures unintelligible to a layman.

A key object is to make possible a heart transplant in a small child—even one too impaired to withstand a conventional heart transplant—and thus avert the impairments in development that would ensue were any but normal pulsatile circulation instated.

Another object is to provide a type valve for use in vascular bypass solid organ transplantation which used in a small child would not require reimplantation or the need for valve replacement until adolescence if not well into adulthood.

Yet another object of the invention is to eliminate the trauma and stress involved in a conventional heart transplant other than that caused by the entry wound which is unavoidable, and in so doing, achieve a graft durability which considerably exceeds that obtainable using conventional surgery.

Another object of the invention is to provide a method for performing a compound vascular bypass heart transplant which is simpler to accomplish in a patient of any age so that general surgeons will be capable of applying it in more rural and remote areas.

An object of the invention and vascular bypass transplantation in general is to make organ transplantation tolerable to patients who would otherwise be considered too impaired to tolerate the conventional procedure, thereby averting the likelihood of continued sickness, the extension of malfunction to the rest of the body, and early death rather than the instatement of the capacity for the patient to realize his full potential and live a normal life.

Compound Vascular Bypass Organ Transplantation

Fully described in copending continuation-in-part application Ser. No. 19/033,348 entitled Vascular Valves and Servovalves—and Prosthetic Disorder Response Systems, the vascular bypass method of organ transplantation avoids incision into either the donor or recipient organs or vessels as required in a conventional, especially a divisional ventricles heart transplant; both recipient and donor organs remaining intact throughout and without transection of the graft organ, or its supply and drainage vessels.

Requiring only connection between the great supply and drainage vessels of the patient and donor organs, here the heart, the compound vascular bypass process for a transplant is simpler, safer, and except for the unavoidable entry wound, considerably less traumatizing for any patient pediatric or adult. The extent of trauma eliminated will often prove sufficient to render patients otherwise too frail to undergo the surgery qualified, thus averting the global degeneration that would otherwise have ensued. Moreover, the greater durability of the graft considerably forestalls if not eliminates the need for later long-term painful entry wounds. The consequence is a considerable improvement in the quality of life.

This major reduction in trauma results in a graft that has not been subjected to the shocks associated with the death of its host, excision, and placement in an immunologically incongruent, albeit ameliorated milieu. The outcome to be expected is graft durability with less if any progressive degradation prior to failure and the need for reimplantation far exceeding the decade or so anticipated for a conventional heart transplant. More specifically, limiting the number of valves used to only the great vessels of the transplant organ blood supply and drainage allows a considerable reduction in the valves required.

This expedites the operation, simplifies it for nonpediatric cardiac and general surgeons, reduces its expense, and making it applicable to patients young or old, some of whom, such as those very young or old or frail, as indicated, would otherwise have been judged unable to tolerate a conventional, especially a ventricles—divisional, heart transplant, leaving these patients consigned to a short life of illness. The elimination of trauma thus results in increased durability of the graft and qualifies patients too frail to undergo the conventional procedure. These are precisely the consequences desired to allow a heart transplant, for example, to be done in a baby or toddler.

The reduction in trauma provides several important benefits, such as qualifying patients who would otherwise be considered too frail to undergo surgery, and likely the improved survival of humanized porcine xenografts, for example, thus contributing to the continued development of this currently experimental approach to the point of widespread acceptance and an unlimited increase in the pool of available graft organs. A donor sustainment center where recently deceased patients are sustained in a condition that for some medical purposes is effectively lifelike should include a pediatric section. The means for sustainment and citation of the pertinent references pursuant thereto is delineated in copending continuation-in-part application Ser. No. 19/033,348.

Otherwise, for the time being, chimerization and immunosuppression notwithstanding, such rejection, compounded with ischemia-reperfusion injury, the distinctions in the immune cells between porcines and humans for example, the possibility of undetected viral infection, the relatively short normal lifespan of other mammals, and the risk of zoonotic transmission, make xenogeneic transplantation, or xenotransplantation, challenging to achieve (see, for example, GaldinaV., Puga Young, G. L., and Seebach, J. D. 2025. "Cytotoxic Responses Mediated by NK [natural killer] Cells and Cytotoxic T [thymus-generated] Lymphocytes in Xenotransplantation," Online, *Transplant International* (Lausanne, Switzerland) 38:13867; Luo, J, Bian, C., Liu, M, Fang, Y., Jin, L, Yu, R., and Huang, H. 2025. "Research on Gene Editing and Immunosuppressants in Kidney Xenotransplantation," *Transplant Immunology* (Amsterdam, North Holland. Netherlands) 89:102184; Ali, A., Kemter, E., and Wolf, E 2024. "Advances in Organ and Tissue Xenotransplantation," Online, *Annual Review of Animal Biosciences* (San Mateo, California) 12:369-390; Cooper, D. K. C. and Cozzi, E. 2024. "Clinical Pig Heart Xenotransplantation—Where Do We Go from Here?," Online, *Transplant International* (Lausanne, Switzerland) 37:12592; Li, J., Xu, Y., Zhang, J., Zhang, Z., Guo, H., Wei, D., Wu, C., and 3 others 2024. "Single-cell Transcriptomic Analysis Reveals Transcriptional and Cell Subpopulation Differences between Human and Pig Immune Cells," *Genes and Genomics* (Seoul, South Korea) 46(3):303-322; Vadori, M. and Cozzi, E. 2024. "Current Challenges in Xenotransplantation," Online, *Current Opinion in Organ Transplantation* (Hagerstown, Maryland) 29(3):205-211; Yan, Y., Zhu, S., Jia, M., Chen, X., Qi, W., Gu, F., Valencak, T. G., and 2 others 2024. "Advances in Single-cell Transcriptomics in Animal Research," Online, [BioMed Central]*Journal of Animal Science and Biotechnology* (London, England) 15(1):102: Arabi, T. Z., Sabbah, B. N., Lerman, A., Zhu, X.-Y., and Lerman, L. O. 2023. "Xenotransplantation: Current Challenges and Emerging Solutions," Online, *Cell Transplantation* (Thousand Oaks, California) 32:9636897221148771; Denner, J. 2023. "Microchimerism, PERV [porcine endogenous retroviruses] and Xenotransplantation," Online, [Multidisciplinary Digital Publishing Institute] *Viruses* (Basel, Switzerland) 15(1):190; Flecks, M., Fischer, N., Krijnse Locker, J., Tunjes, R. R., and Godehardt, A. W. 2023. "Analysis of PERV-C [porcine endogenous retrovirus class C (ectopic virus that infects only pig cells)] Superinfection Resistance Using HA[hemagglutinin]-tagged Viruses" Online, *BioMed Central Retrovirology*. (London, England) 20(1):14; Lei, T., Chen, L., Wang, K., Du, S., Gonelle-Gispert, C., Wang, Y., and Buhler, L. H. 2022. "Genetic Engineering of Pigs for Xenotransplantation to Overcome Immune Rejection and Physiological Incompatibilities: The First Clinical Steps," Online, *Frontiers in Immunology* (Lausanne, Switzerland) 13:1031185; Lopez, K. J., Cross-Najafi, A. A., Farag, K., Obando, B., Thadasina, D., Isidan, A., Park, Y., and 3 others 2022. "Strategies to Induce Natural Killer Cell Tolerance in Xenotransplantation," *Frontiers in Immunology* (Lausanne, Switzerland) 13:941880; Heo, Y., Cho, Y., Oh, K. B., Park, K. H., Cho, H., Choi, 1., Kim, M., and 3 others 2019. "Detection of Pig Cells Harboring Porcine Endogenous Retroviruses in Non-human Primate Bladder after Renal Xenotransplantation," Online, [Multidisciplinary Digital Publishing Institute]*Viruses* (Basel, Switzerland) 11(9): 801).

Given the precarious condition of these patients and the considerable trauma of a conventional heart transplant, the fundamental reduction in trauma due to the elimination of the extensive dissection, cardioplegia, and cardiopulmonary bypass for the recipient and the avoidance of cold storage and ischemia-reperfusion injury for the graft organ involved in conventional heart transplant, especially one ventricles divisional, should materially improve the odds for a better outcome. "Looking ahead, designing systematic trials in xenotransplanation, including the definition of acceptable eligibility criteria for such high-risk transplants, will be an immense challenge . . . " (Böhmig, G. A., Diebold, M., and Budde, K. 2024. "Opinions on the Future of Clinical Pig Kidney Xenotransplantation," Online, *Transplant International* (Lausanne, Switzerland) 37:13475).

Essentially, using the compound vascular bypass method leaves only the unavoidable midsternal thoracotomy, clamshell, or hemiclamshell entry wound, for example, as the source of injury and persistent pain. That whether for an allograft or a xenograft, a compound vascular bypass heart transplant does not involve the physical joining by direct anastomosis of the donor and recipient hearts means that at least anatomically and aside from physiology, the hearts need not match in size or in shape is another significant advantage. Liberalization in the relative size of the graft also equates to liberalization of its positioning within the body.

A fundamental advantage in the use of an implanted disorder response system is intermittent or continuous monitoring for signs of rejection or infection to which the system is able to respond immediately by pipe-targeting counteractants directly to the affected site or sites as well as systemically when the patient is far from a clinic. The combination of a surgical method that eliminates much of the trauma and organ ischemia-reperfusion injury and the implanted automatic disorder response system to guard against hyperacute rejection should materially facilitate progress in the field of organ transplantation.

The highly distensible valves described can be used to accomplish any other organ transplant in small children while the simplification in heart transplantation applies to patients of any age. This application relegates the more detailed factors pertaining to compound vascular bypass organ transplantation to copending continuing application-in-part, Ser. No. 19/033,348, and will no more than review the information necessary to apprehend the functioning of the valves described herein devised to considerably increase the accommodation of growth in small children compared to the ordinary vascular valves described in the copending continuation-in-part application which already supported growth but only according to the thickness of the foam layer lining the valves.

Born with hearts so malformed as to defy surgical repair that would impart the normal pulsatile circulation essential for normal development, vascular bypass heart transplantation should not just save lives but ameliorate if not eliminate the debilitating health problems that may follow a conventional heart transplant, and ideally, make possible the full realization of the patient's potential. Vascular bypass organ transplantation applicable to any solid organ, the same may be said for the early replacement of any other organ any one or combination of which would adversely affect the development of a young patient.

In addition to the considerable reduction in surgical trauma, the advantages of vascular bypass heart transplantation should also eliminate the need for cardiopulmonary support, cardioplegia, and general anesthesia. Significantly, the reduction in trauma can make patients otherwise judged surgery-intolerant candidates for a life-saving and quality of life operation. In patients at any age, compound vascular bypass heart transplantation is meant to considerably extend and preferably eliminate the period preceding the eventual need for reimplantation—certainly for a period much longer than the ten years currently ascribed to the severely traumatizing partial or divisional heart or ventricles transplant conventionally performed.

At the same time, by limiting the number of valves to only the blood supply and drainage vessels, the number needed is reduced from eighteen to ten, specifically those needed on the right and left pulmonary arteries, the aorta, and the superior and inferior venae cavae of both recipient and donor. This simplification reduces not only the duration but the stress on the patient and the cost of the operation as well as shortens the learning curve for the practitioner. In vascular bypass organ transplantation, the blood supply and drainage of the donor organ are directly connected to the corresponding vessels of the recipient organ by means of vascular valves.

These allow the apportionment of blood blended between the donor and recipient organ to be adjusted from zero percent in the recipient organ which is then removed to one hundred percent in the donor organ made integral in the circulatory system of the recipient. The number of such connections needed to transplant the heart are the ten specified. The donor having been sustained in the donor sustainment center on life support commencing prior to death, the blood flow pattern this entails is depicted at the midway point in FIG. 1 as the midway position of the valves attest. In a donor sustainment center, also described in copending continuation-in-part application Ser. No. 19/033,348, entitled Vascular Valves and Servovalves—and Prosthetic Disorder Response Systems, immunological compatibility data pertaining to the donors and recipients will have been collected and recorded upon their arrival.

In the context of vascular bypass organ transplantation, the term 'life support' does not equate to, although with prospective graft organs other than the heart, it can be inclusive of, cardiopulmonary bypass and external membrane oxygenation when necessary. Normothermal and pulsatile preservation preferred, prospective graft hearts may be kept beat-synchronized within the deceased donor with the aid of a pacemaker/cardioverter defibrillator. Preservation is addressed in copending continuation-in-part application Ser. No. 19/033,348.

At the start of the vascular bypass transplant, the vascular servovalve in the upper right-hand corner would have been positioned entirely to the left, constraining the heart outflow to the recipient and the valve on the upper left would have been entirely to the right, constraining outflow to the recipient. As the valve in the upper right moves toward the right and the that in the upper left moves more to the left, the proportion of blood between donor and recipient is gradually changed from intervening levels of an increasing blend to a complete blend of recipient and donor blood. Having been gradually and guardedly acclimated to one another with the fully blended blood now circulating in the recipient and in the donor organ, positioning the donor heart in the recipient is immunologically uneventful.

Accordingly, to replace the organ, the blood coursing through the organ is gradually changed from that of the donor to a blend of that of the recipient and the donor whose compatibility had previously been determined and reinforced as necessary. Only the main blood supply and drainage vessels of the donor and recipient hearts need be valved and connected together by blood delivery catheters, or bloodlines. While the reciprocal cross-circulation had been in progress, the donor heart would have fed to and received blood from the recipient as shown; the severed stumps shown on the donor heart to the left denote removal from the body of the donor heart for placement in the recipient where it will remain at the center of the recipient circulatory system—at the same time, the heart of the recipient is removed from the recipient for discarding or retention as a pathology specimen.

The donor having been in the donor sustainment center for an interval prior to the operation has been administered drugs to condition the donor heart and facilitate acceptance by the eventual recipient. The direction of reciprocal cross-circulation blood flow also takes advantage of the superior ejection fraction of the healthy donor as opposed to the impaired recipient heart. From the outset, the pulmonary circulation is channeled to support the lungs of the recipient with immunologically uncompromised blood which will progressively be blended with the blood of the donor, the rate thereof controlled by the automatic disorder response system as programmed and monitored by a diagnostician and/or intensivist who can manually intervene at any time. For these reasons, the direction of blood flow shown in FIG. 1 is shown as moving from the donor to the recipient who is the party and the greater mass of tissue to be acclimated to the graft organ also acclimated as soon as possible.

The detection by the implanted sensors which report to the automatic system of a rejection reaction intense as to cause concern can be programmed or manually controlled to interrupt the continued adjustment in flow that blends the blood of the donor with that of the recipient, can stop the reciprocal cross-circulation for a time, or in the event of an unpredictable crisis, shut down the procedure entirely. However, due to the preliminary and midoperative diagnostics and treatment of both recipient and donor with immune tolerance inducing, antimicrobial, and anti-inflammatory medication as necessary, the expectation for an intense reaction is low.

Once blood flow has been entirely diverted by being completely shut off from the native organ of the recipient and exclusively passed through the donor organ, the donor organ will have been rendered compatible with the recipient, at which time the native heart of the recipient, along with its vascular valves, is removed. The valves of the donor organ, however, are not removed but rather implanted with the graft so that the valve accessory channels will remain to allow the automatic implanted prosthetic disorder response system to directly target drugs to the graft organ and its vasculature in response to signals supplied to the system control microprocessor by implanted sensors.

Figure 2:
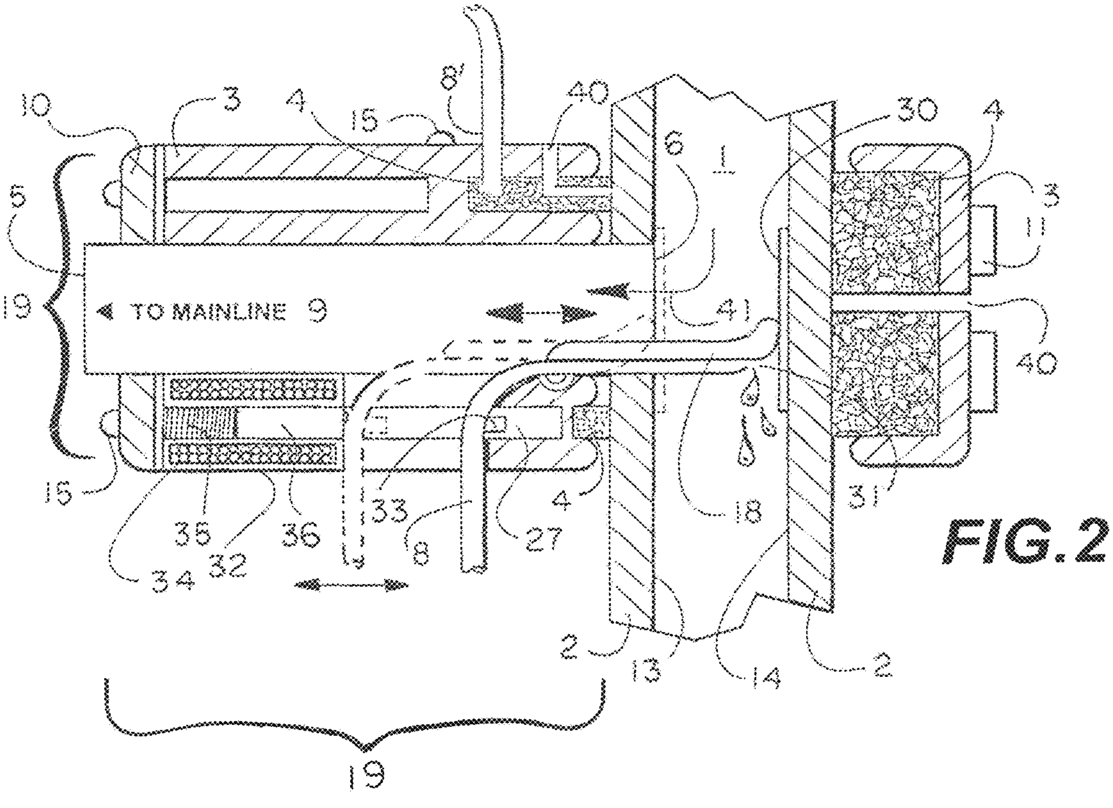
FIG. 2 shows an ordinary vascular valve for use in a vascular bypass solid organ transplant which can accommodate growth in accordance with the thickness of the foam lining the outer shell of the vessel.

Valves that incorporate one or more druglines such as 8 in FIG. 2 which supply a vessel are incorporated in the implant for follow-up automatic drug administration by the implanted prosthetic disorder control system at any place and time, and for this reason, positioned to avert a crisis should it arise. Accordingly, all valves used to perform an organ transplant are included in the implant; vascular valves are not made with disengageable removable accessory channels as would allow only the disengageable accessory channel with drugline to be retained in the implant while allowing the better part of the valve to be removed at the end of the operation.

From the standpoint of providing the patient with comprehensive post-discharge care, automatically targeted drug delivery by the implanted disorder response system is not limited to the vessels of one or more graft organs, especially with the multimorbid disease more likely where a major organ had malfunctioned and/or the patient is elderly. Two means for controlling drug delivery other than through a vascular valve are at control at the implanted drug reservoir and delivery through a nonjacketing side-entry connector such as that shown in FIG. 4. Stationary or moving, at any degree of chute extension into the lumen, the pressure of drug delivery can be controlled at the reservoir.

Figure 4:
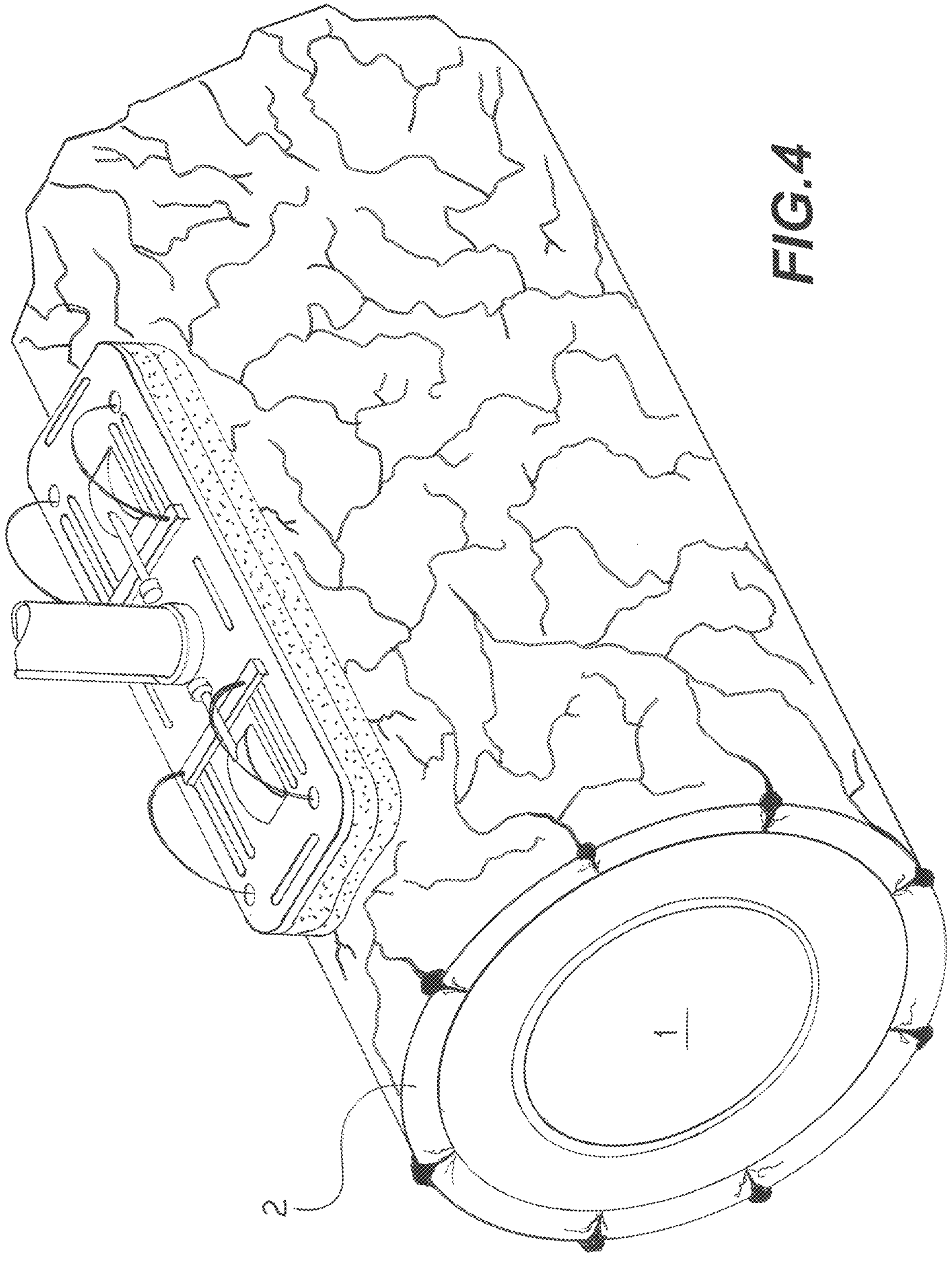
FIG. 4 shows a nondistensible nonjacketing side-entry connector as described in U.S. Pat. No. 11,013,858, entitled Nonjacketing Side-entry Connectors and Prosthetic Disorder Response Systems, for connection directly to the surface of an organ or great vessel, here the latter, used to replace the drugline of a vascular valve removed along with the defective native organ at the conclusion of a vascular bypass organ transplant to allow the continued automatic delivery of drugs by the implanted disorder response system where the vascular valves had best been removed.
Figure 5:
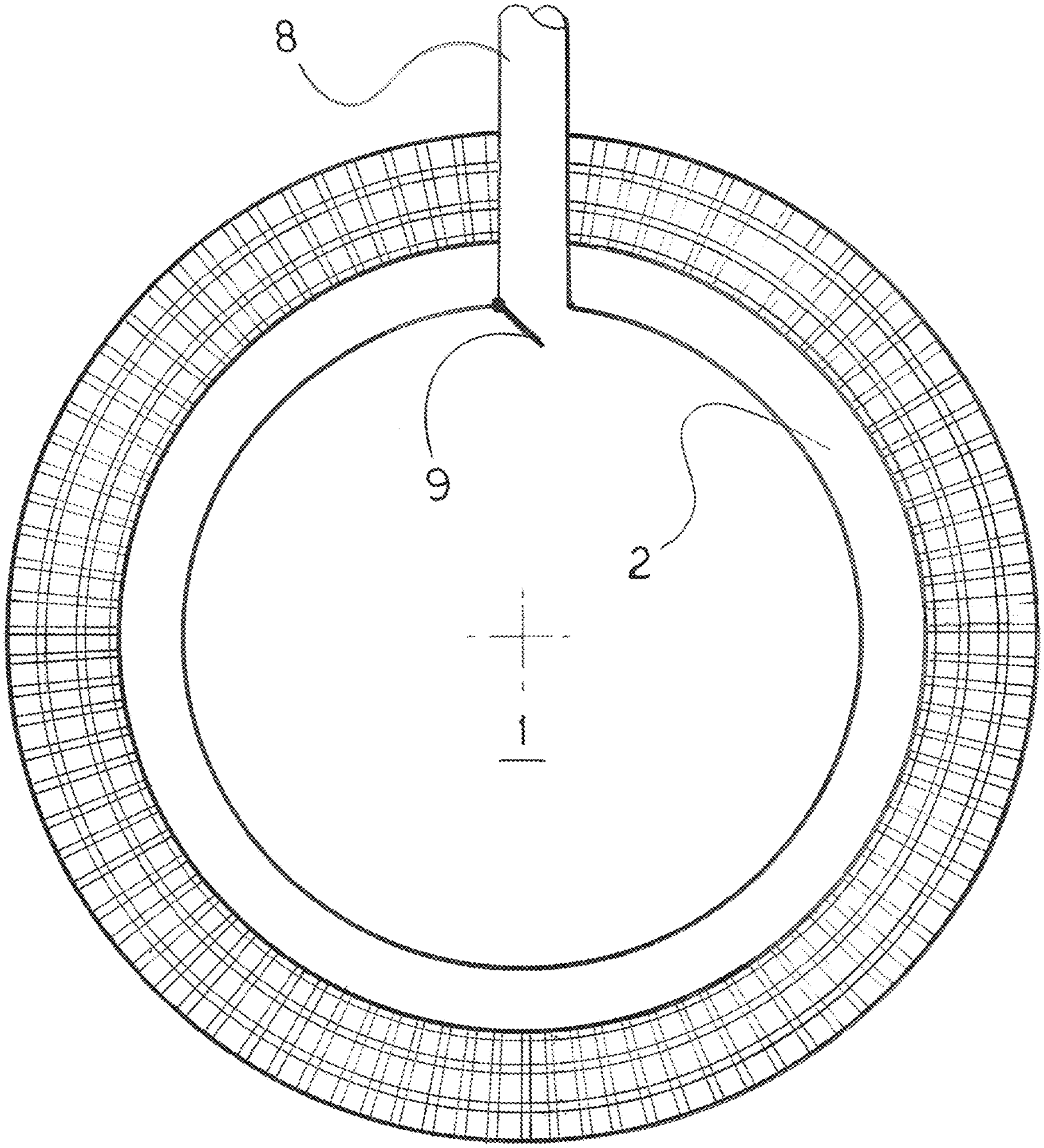
FIG. 5 shows a distensible vessel encircling collar for replacing the drugline of a vascular valve removed along with the defective native organ at the conclusion of a vascular bypass organ transplant to allow the continued automatic delivery of drugs by the implanted disorder response system where the vascular valves had best been removed.

Drug delivery through the drug delivery mountings depicted in FIGS. 3 thru 5 suitable for replacing a valve used to accomplish an organ transplant, for example, can be targeted to any specific vessel or level along the vessel greater than an arteriole, but usually to the blood supply or outflow of an organ which demands treatment, or has been transplanted. Less specific situation is needed to target the pulmonary or systemic circulation. In multimorbid disease, the automatic disorder control system can simultaneously target medicinals to any number of primary and/or secondary sites in the body where the object is to attain the optimal overall homeostasis which can be provided for the patient.

That is, another point for prosthetic disorder system microprocessor automated and scheduled control over the targeted automatic dispensing of medication at a specific dose is the controllable stopcock at the outlet of each drug reservoir implanted subcutaneously, usually in the pectoral region. Since full retraction of the flow diversion chute, part number 18 in FIG. 2, causes all blood to flow through the substrate vessel, drug delivery by this means necessitates extending the chute into the lumen, the extent of which determines the volume and rate of the flows through and past the chute. Full extension of the chute redirects all blood flow through the valve sidestem. For brief drug delivery to the supply and drainage vessels of most organs, native or transplanted, this inherent link should prove inconsequential.

However, with cardiac vessels, this may not be so; when handled, cardiac vessels are subject to the inducement of adverse events which control at the reservoir or a nonjacketing side-entry connector is not. When the valve has been retained for some other reason, concern regarding the inducement of an adverse event is dispelled by implanting a disorder response system automatically controlled means for resynchronization in the form of a conventional pacemaker/cardioverter-defibrillator. A nonjacketing side-entry connector omits the intrusion factor while allowing full control at the reservoir.

Control at the reservoir reduces the risk of inducing an adverse cardiac event and offers the additional advantage of allowing the wire that would otherwise be needed to control each diversion chute to be removed. In a multimorbid patient requiring numerous drugs, three means for controlling the release of drugs—at the reservoir, the diversion chute, or nonjacketing side-entry connector, can be incorporated into the prescription program executed by the system master control microprocessor. Accordingly, accomplishing the dispensing of drugs by a drug reservoir through a nonjacketing side-entry connector allows a reduction in the number of wires from the master control microprocessor to the valve and number of intact valves that need to be left in the patient.

As described in U.S. Pat. Nos. 11,759,186; 11,013,858; and in copending nonprovisional application Ser. Nos. 19/033,348 and 17/689,880, a hierarchical control system comprising a number of control arms or channels, each provided with sensors and effectors, can have assigned to each arm or channel a separate morbidity, and coordinate treatment by each channel to achieve an overall optimal state of homeostasis for the specific patient. Seen thus, a prosthetic disorder response system is not properly thought of as necessarily associated with organ transplantation but has a place in the treatment of any or all serious chronic diseases mono- or multimorbid, especially with prescription adherence-undependable patients.

Drawing FIG. 1 also represents the ending rather than midway blood flow pattern upon the completion of an operation to add a second heart to that materially impaired where the two working together can achieve an adequate ejection fraction. The fact that in an assist heart transplant the graft organ can be less than perfect increases the pool of available graft organs and poses a solution to the unaffordability of ventricular assist devices in third world countries. In a double heterotopic vascular bypass heart transplant, the recipient heart is left in place and the donor heart added to assist it. Copending continuation-in-part application Ser. No. 19/033,348 specifies different positionings to accommodate a second, usually smaller, heart in the body of the recipient.

For prompt action in an urgent circumstance, the valves used to transfer the donor organ into the circulatory system of the recipient are nonsparking and highly damped solenoid-driven. Solenoid-driven valves can also be used to reduce the duration of the operation for a patient who is severely debilitated. Preferably, however, to minimize the shock for the graft organ and the recipient following the placement of an alien organ, servomotor-driven valves are used to render the process as gradual with immune tolerance inducing medication as necessary.

To this end, all vascular valves incorporate at least one accessory channel into which a drugline can be inserted to directly deliver any liquid drug, to include immune tolerance-inducing as necessary, into the valve and the organ it serves whether prior, during, or following the surgical procedure. The immature immune system in the very young and the relative brevity of the operation will usually favor the use of plunger solenoid—rather than servomotor-driven valves. Moreover, the wire of the winding or coil in solenoid-driven valves can be made of silver, thus allowing a considerable miniaturization of the valve as compared to a valve made with a copper winding.

While a vascular bypass organ transplantation can be administered or supplemented using manually performed diagnostic and medicinal support, as indicated, the organ transfer is preferably administered primarily by an automatic prosthetic disorder response system, which described in copending applications-in-part Ser. Nos. Ser. No. 19/033,348 and 17/689,880, entitled Prosthetic Disorder Response Systems filed on 8 Mar. 2022, is provided with rejection sensors which allow it to optimize the rate of transfer between circulatory systems immediately and therewith, optimize the acclimation of the recipient to the donor organ and the donor organ to its new milieu.

Unlike dependency upon diagnostic laboratory results that take time to obtain biopsy samples and become available only after an interval, the automatic implanted system instantly responds with the directly targeted delivery of medication to the donor graft organ implanted in the recipient. Most often it will be sufficient to implant the automatic control system in the recipient but not the donor who will have been available in the sustainment center for diagnostic testing prior to initiating the transplant. While manual diagnostics can be used during the transplant, an implanted system also provides the considerable advantage of continuing to provide postoperative treatment regardless of his location after the patient has departed.

The donor and recipient having been sufficiently matched prior to the transplant operation, depending upon its severity, the detection of rejection will cause the control system to suspend the continued progression of the vascular servovalves in administering the organ transfer until an adequate degree of immunological stability has been instated. During this interval the implanted system automatically detects the need for and releases medication to reduce the intensity of the rejection reaction. When not administered automatically, an immunologist, diagnostician, intensivist, anesthesiologist, or group of specialists monitor the operation to control the organ transfer.

Postoperatively, however, an implanted prosthetic disorder response system can continue to administer the release of medication to the graft, and/or in multimorbid disease, the rest of the body through the vascular valves immediately regardless of the time or location. Valves can be positioned on vessels uninvolved in organ transplantation. Especially in the follow-up of comorbid disease, valves can be connected to the pulmonary or systemic circulation. In a severely debilitated patient, this wider scope of immediate treatment supports not only a better environment for one or more graft organs but bodes favorably for the overall health of the patient.

Thus, once the operation has been completed, to allow the follow-up direct targeting of drugs such as anti-inflammatory, antimicrobial, or immune tolerance-inducing to the graft organ by the fully implanted prosthetic disorder response system, unless contraindicated for compelling reasons, the valves are left in place.

A conventional heart transplant usually consisting of actually transplanting only the inferior half of the heart containing the ventricles—which is severely traumatic, debilitating, and has long-term adverse consequences—the donor and recipient hearts must be not deviate more than a little in overall size. This is a limiting factor that reduces the number of usable replacement hearts. In contrast, by not involving the need for a matching in size, the vascular bypass technique provides unlimited latitude in the relative size of the donor and recipient hearts and in so doing, further increases the pool of replacement hearts that are usable.

That is, since the second heart can be either significantly smaller or larger than that of the recipient, when a second heart is implanted to assist that native, this factor serves to liberalize the pool of available graft hearts. The elimination of incisional trauma, especially with respect to the common divisional technique, does away with the additional shocks to the donor organ of the death of its host and excision, and the automated and/or manual administration of immune tolerance-inducing medication reduces the additional shock of entry into the immunologically alien milieu of the recipient.

As documented in copending application Ser. No. Ser. No. 19/033,348, the trauma associated with conventional, especially partial or divisional heart transplantation, is suspected to be responsible for cardiac allograft vasculopathy and has also been found to result in a disparity in growth rate of the semilunar valves, both of which signal the impending end to the useful life of the graft (see, for example, Nissen, T. E., Chung, S., Brown, A., Sanders, E., Parashar, N., Knecht, K. R., Rajab, T. K., and Qasim, A. 2025. "Semilunar Valves in Pediatric Orthotopic Heart Transplants Grow at a Slower Rate than Controls," Pediatric Cardiology (New York, New York) May 12; Zhou, P., Dong, Z., Hu, X., Yang, S., Wang, J., Ma, X., Tang, Y., and 8 others 2025. "Incremental Value of Multiparametric Cardiac Magnetic Resonance Imaging for Non-invasive Identification of Significant Acute Cardiac Allograft Rejection: A Prospective and Biopsy-proven Study," Online, European Heart Journal. Cardiovascular Imaging 26(5):886-894; Rajab, T. K., Abdelrahman, M., Schwartzenburg, E. J., Aykut, B., Turek, J. W., and McVadon, D. H. 2024. "Semilunar Valve Growth and Function 10 Years after Infant Heart Transplantation: Predicting Long-term Outcomes of Partial Heart Transplants," Online, Pediatric Transplantation (Copenhagen, Denmark) 28(3): e14746; Sethi, N., Doshi, A., Doshi, T., Cross, R., Cronin, I., Amin, E., Kanter, J., and 4 others 2020. "Quantitative Cardiac Magnetic Resonance T2 Imaging Offers Ability to Non-invasively Predict Acute Allograft Rejection in Children," Online, Cardiology in the Young (Cambridge, England) 30(6):852-859).

Both cardiac allograft vasculopathy if not a gradual metaplastic transition to carcinoma and/or sarcoma and the development of a disparity in the growth rate of the semilunar valves compared to the rest of the heart arise gradually over a significant interval. Accordingly, the durability of a graft heart in the short term of less than as many as ten years following implantation of a graft delivered by transport is inadequate as a criterion for predicting a successful outcome.

More specifically, that " . . . the modified heart preservation method did not increase the risk of mortality compared to the conventional method" is of little consequence since except in a very elderly patient and certainly in a child, once the sustainment center concept with no interruption in normothermal graft perfusion has been implemented, alternative means of graft acquisition should prove acceptable only where the donor had died unexpectedly (Shang, X., Zhang, C., Wang, Y., Liu, M., Zhong, Y., and Dong, N. 2025. "Heart Transplantation: Comparing the Impact of Modified Heart preservation with Conventional Methods," Online, Scientific Reports (London, England) 15(1):2937).

Unless donor sustainment centers are also established at distances from major medical centers, that vascular bypass organ transplantation is simpler to perform and provides more durable results will be denied the full realization of its potential for a significant proportion of the public. However, even with temperature-controlled continuous perfusion graft preservation, it should still supplant conventional surgery.

That is, despite a reduction in long-term graft durability, when deaths occur outside a hospital before life support can be initiated, compound vascular bypass organ transplantation will still rank as materially superior to conventional organ transplantation with graft transport to a medical center using the Organ Care System or preservation in cold storage (see, for example, Jernryd, V., Stehlik, J., Metzsch, C., Lund, L. H., Gustav Smith, J., Andersson, B., Perez, R., and Nilsson, J. 2025. "Donor Age and Ischemic Time in Heart Transplantation—Implications for Organ Preservation," Online, Journal of Heart and Lung Transplantation 44(3): 364-375; Alomari, M., Garg, P., Yazji, J. H., Wadiwala, I. J., Alamouti-Fard, E., Hussain, M. W. A., Elawady, M. S., and Jacob, S. 2022. "Is the Organ Care System (OCS) Still the First Choice with Emerging New Strategies for Donation after Circulatory Death (DCD) in Heart Transplant?," Cureus (Palo Alto, California) 14(6):e26281; Schaink, A., Gajic-Veljanoski, O., Wells, D., and Holubowich, C. [Ontario Health (Quality)]2020. "Portable Normothermic Cardiac Perfusion System in Donation after Cardiocirculatory Death: A Health Technology Assessment," Ontario Health Technology Assessment Series (Toronto, Ontario, Canada) 20(3):1-90; Sunjaya, A. F. and Sunjaya, A. P. 2019. "Combating Donor Organ Shortage: Organ Care System Prolonging Organ Storage Time and Improving the Outcome of Heart Transplantations," Online, Cardiovascular Therapeutics (London, England) 2019:9482797).

An appreciable improvement in graft durability should prove significant in obtaining success following heart transplantation or retransplantation in severely impaired children (see, for example, (Singh, T. P., Profita, E. L., Rycus, P., Thiagarajan, R., and Gauvreau, K. 2021. "Risk Factors for Severe Primary Graft Dysfunction in Infants following Heart Transplant," Online, Journal of the American Heart Association (Oxford, England) 10(13):e021082; Profita, E. L., Gauvreau, K., Rycus, P., Thiagarajan, R., and Singh, T. P. 2019. "Incidence, Predictors, and Outcomes after Severe Primary Graft Dysfunction in Pediatric Heart Transplant Recipients," Online, Journal of Heart and Lung Transplantation (New York, New York) 38(6):601-608; Bryant, R. 3rd, Rizwan, R., Villa, C. R., Zafar, F., Wells, D., Chin, C., Lorts, A., and Morales, D. L. 2018. "Transplant Outcomes for Congenital Heart Disease Patients Bridged with a Ventricular Assist Device," Annals of Thoracic Surgery (Amsterdam, North Holland, Netherlands) 106(2):588-594; Jayakumar, K. A., Addonizio, L. J., Kichuk-Chrisant, M. R., Galantowicz, M. E., Lamour, J. M., Quaegebeur, J. M., Hsu, D. T. 2004. "Cardiac Transplantation after the Fontan or Glenn Procedure," Journal of the American College of Cardiology (New York, New York) 44(10):2065-2072).

The state of pediatric heart transplantation is well covered in the literature (see, for example, (Everitt, M. D., Pahl, E., Koehl, D. A., Cantor, R. S., Kirklin, J. K., Reed, A. C., Thrush, P., and 4 others 2025. "Clinical Outcomes after a Biopsy Diagnosis of Antibody-mediated Rejection in Pediatric Heart Transplant Recipients," Journal of Heart and Lung Transplantation (New York, New York) 44(1):82-91; Rivero-Santana, B., Balbacid-Domingo, E., Abelleira-Pardeiro, C., Labrandero de Lera, C., Arreo Del Val, V, Jiménez-Valero, S., Fernández-Velasco, M., and 2 others 2025. "Microcirculatory Dysfunction and Its Role in Diagnosing Acute Rejection in Pediatric Heart Transplantation: A Pilot Study," Online, Diagnostics (Basel, Switzerland) 15(5):545; Dipchand, A. I. and Webber, S. A. 2024. "Pediatric Heart Transplantation: Looking Forward after Five Decades of Learning," Pediatric Transplantation (Copenhagen, Denmark) 28(1):e14675; Martens, S., Tie, H., Kehl, H. G., Tjan, T. D., Scheld, H. H., Martens, S., and Hoffineier, A. 2023. "Heart Transplantation Surgery in Children and Young Adults with Congenital Heart Disease," Online, Journal of Cardiothoracic Surgery (London, England) 18(1):342; Barnes, A. and Gibson, W. 2021. "Pediatric Heart Transplant," Seminars in Pediatric Surgery 30(2):151039; Godown, J. and Lambert, A. N. 2021. "Minimizing the Risk of Severe Primary Graft Dysfunction in Infant Heart Transplant Recipients: Time for a Paradigm Shift," Online, Journal of the American Heart Association (Oxford, England) 10(13):e022184; Dipchand, A. I. and Laks, J. A. 2020. "Pediatric Heart Transplantation: Long-term Outcomes," Online, Indian Journal of Thoracic and Cardiovascular Surgery (New Delhi, India) 36(Suppl 2):175-189; D'Addese, L., Joong, A., Burch, M., and Pahl, E. 2019. "Pediatric Heart Transplantation in the Current Era," Current Opinion in Pediatrics (Philadelphia, Pennsylvania) 31(5):583-591; Reinhardt, Z. 2019. "Paediatric Heart Transplantation: An Update," Archives of Disease in Childhood (London, England) 104(12):1216-1222; Ybarra, A. M. and Castleberry, C. 2019. "Practice Variability in Pediatric Heart Transplantation: Opportunities for Collaboration," Online, Translational Pediatrics (Hong Kong, China) 8(4):339-341; Dipchand, A. I. 2018. "Current State of Pediatric Cardiac Transplantation," Online, Annals of Cardiothoracic Surgery (Hong Kong, China) 7(1):31-55; Schweiger, M., Stiasny, B., Dave, H., Cavigelli-Brunner, A., Balmer, C., Kretschmar, O., Bürki, C., and 2 others 2015. "Pediatric Heart Transplantation," Online, Journal of Thoracic Disease (Hong Kong, China) 7(3):552-559; Conway, J., Manlhiot, C., Kirk, R., Edwards, L. B., McCrindle, B. W., and Dipchand, A. I. 2014. "Mortality and Morbidity after Retransplantation after Primary Heart Transplant in Childhood: An Analysis from the Registry of the International Society for Heart and Lung Transplantation," Journal of Heart and Lung Transplantation (New York, New York) 33(3):241-251).

Another probability is that a uniformization in practice among practitioners will result in uniformly improved long-term outcomes (O'Connor, M. J., Lin, K. Y., and Rossano, J. W. 2020. "Measuring Quality in Pediatric Heart Transplantation—An Important but Challenging Goal," Online, Journal of the American Medical Association Network Open (Chicago, Illinois) 3(11):e2024137; Singh, T. P., Mehra, M. R., and Gauvreau, K. 2020. "Characteristics Associated with High-performing Pediatric Heart Transplant Centers in the United States from 2006 to 2015," Online, Journal of the American Medical Association Network Open (Chicago, Illinois) 3(11):e2023515; Singh, T. P., Mehra, M. R., and Gauvreau, K. 2019. "Long-term Survival after Heart Transplantation at Centers Stratified by Short-term Performance," Online, Circulation: Heart Failure (Hagerstown, Maryland) 12(11):e005914; Singh, T. P. and Gauvreau, K. 2018. "Center Effect on Posttransplant Survival among Currently Active United States Pediatric Heart Transplant Centers, American Journal of Transplantation (New York, New York) 18(12):2914-2923).

Surgical Procedure

All donors brought from elsewhere within the hospital or medical center or otherwise transported to the donor sustainment center must have been placed on life support prior to death. The continued support required includes the preservation of body temperature and hormonal function, for example, and is specified with citations to the literature in copending continuation-in-part application Ser. No. Ser. No. 19/033,348, which also lays out the technique used to apply vascular valves.

To elevate the origin of the coronary arteries sufficiently above the aortic root to make room for the donor aortic vascular valve to directly supply the coronary arteries in the donor or graft heart from the aorta, all prospective donor hearts upon arrival at the sustainment center or shortly thereafter must have performed on them a coronary artery bypass graft. This does not apply to the graft organ of the recipient whose defective heart will be discarded so that the aortic vascular valve of the recipient can overlie to occlude the coronary arteries of the recipient aorta. The new origin of the coronary arteries in the donor must be just superior to the vascular valve—another artery such as the mammillary which will not be included in the graft must not be used. Since an eventual vascular valve might be either solenoid or servomotor-driven, the valve is not placed until the transplant is performed.

Nestled in the concavity of the aortic arch and crowded by the neighboring anatomy such as the bronchi, positioning of the pulmonary valves to transfer the pulmonary circulation from the recipient to the donor directly from the pulmonary trunk is not feasible; instead, once branched and emerged as more accessible, the right and left pulmonary arteries of the donor and recipient are valved separately. Recipient and donor superior and inferior venae cavae are then valved.

Catheteric bloodlines connecting corresponding valves in the donor and recipient transfer the circulation from the recipient organ into the graft in the donor. The donor organ has then been transferred from the circulatory system of the donor into that of the recipient. In an urgent circumstance, solenoid valves are used; preferably however, the process of transfer between circulatory systems is carried out gradually under constant detailed surveillance exercised by both the prosthetic disorder response system and the attending diagnostician,

DESCRIPTION OF THE PREFERRED EMBODIMENTS

While the vascular valves described in parent application Ser. Nos. 16/873,914 and 19/033,348 afforded expandability for growth, herein are described highly distensible vascular valves devised to expand to a greater extent, from early childhood to late adolescence if not adulthood without the need for reentry and replacement. Also described here is a simplified method for vascular bypass heart transplantation which requiring the placement of valves on only the blood supply and drainage, considerably reduces the number of vascular valves required.

Provided herein are valves for use in pediatric patients in cardiac, urological, hepatological, or pulmonary contexts. The disclosed valves are devised for use in a bypass vascular organ transplant as delineated in detail in copending continuation-in-part application Ser. No. 19/033,348. As set forth herein, the valves are highly distensible and also applicable to the replacement of any other solid organ or gland in a child.

However, in nondistensible form, the valves and method are no less suitable for use by a urological, hepatological, or pulmonary surgeon, for example, in an adult, often one elderly affected by multimorbid disease, and less tolerating of the conventional procedure.

As described herein, in a small child, the desirability of removing the valves and replacing them with directly pipe-targeted automatic postoperative drug delivery lines by the implanted disorder response system is met with independent drug delivery lines. The vascular bypass method is also applicable to living or deceased donor partial or divisional liver or lung transplantation, or humanized porcine organ xenotransplantation, for example, as well as to normothermal pulsatile circulation-sustained deceased donor composite tissue transplantation, for example.

Described are distensible growth-accommodating vascular valves for heart transplantation in pediatric patients which for replacement a heart that cannot be adequately repaired conventionally, thereby facilitating aversion of a global impairment in development of the patient. Optimizing operative tolerability, the process used, and vascular bypass heart transplantation eliminates surgical trauma of both donor and recipient hearts, the need for cardiopulmonary bypass, cardioplegia, general anesthesia, and graft organ anoxia and degradation before and after harvesting and storage. Advantageously, this can reduce late-term cardiac allograft vasculopathy and disparities in semilunar valve growth as causes of graft failure. This elimination of trauma results in a graft of considerably greater durability than can be provided by conventional heart transplantation. This disclosure also provides for the administration of drug delivery, preferably executed automatically under the control of a fully implanted prosthetic disorder response system. Drugs delivered via druglines to these vascular valves and servovalves can directly target medication to nidi, anastomoses, or any other trouble spots.

Extremely expandable or distensible vascular valves made to expand in step with growth in a small child and thus allow the avoidance of a later need for reentry and replacement of a graft organ differ from the conventional valves are described in copending continuation-in-part application Ser. No. 19/033,348 in some basic respects. For example, there is no metal or polyetheretherketone, for example, blood outflow channel with a trepan at its leading edge to draw out a plug of tissue from the substrate vessel to pass through the valve flow diversion chute into the lumen of the vessel. Instead, the plug of tissue is removed using a separate catheter with a razor-sharp front edge connected to an aspirator.

A loss of blood is averted simply by covering over the opening or ostium with a thumb. In an ordinary valve, the degree to which the valve will accommodate growth depends upon the thickness of the foam lining the outer shell, and the blood outflow channel is sized at an intermediate, slightly larger than current caliber to best fit the increasing volume and rate of blood flow as the patient grows. In a distensible valve, part number 19 in FIG. 3, rather than the trepan leading edged ordinary valve shown in FIG. 2, is itself the sidestem or blood outflow channel. As depicted in FIG. 1, the orientation of both ordinary and growth-accommodative valves as to upright, inverted, or reversed, as sending or receiving, as well as the selectability of rotational angle and level along a substrate vessel is unrestricted. This versatility of positioning is highly advantageous in a small child.

Polyurethane foam subject to chemical breakdown when exposed to water, the surface of foam 4 has a vapor-deposited, or sputtered, coating of highly expandable and fully compliant parylene to isolate it from moisture (see, for example, Ji, H., Shi, X., and Yang, H. 2024. "Recent Advances in Polyurethane for Artificial Vascular Application," Online, Polymers (Basel, Switzerland) 16(24):3528; An, Z. W., Xue, R., Ye, K., Zhao, H., Liu, Y., Li, P., Chen, Z. M., and 2 others 2023. "Recent Advances in Self-healing Polyurethane Based on Dynamic Covalent Bonds Combined with Other Self-healing Methods," Online, Nanoscale (Cambridge, England) 6; 15(14):6505-6520; Zhou L, Zhang L, Li P, Maitz M F, Wang K, and 7 others 2022. "Adhesive and Self-healing Polyurethanes with Tunable Multifunctionality," Online, Research (Washington, D.C.) 2022:9795682; Li, Z., Yu, R., and Guo, B. 2021. "Shape-memory and Self-healing Polymers Based on Dynamic Covalent Bonds and Dynamic Noncovalent Interactions: Synthesis, Mechanism, and Application," American Chemical Society Applied Bio Materials (Washington, D.C.) 4(8):5926-5943; Xu, H., Tu, J., Li, P., Liang, L., Ji, J., Xiang, G., Li, H., and 2 others 2021. "Main-side chain Hydrogen Bonding-based Self-healable Polyurethane with Highly Stretchable, Excellent Mechanical Properties for Self-healing," Acid-Base Resistant Coating," Macromolecular Rapid Communications (Weinheim, Germany) 42(20):e2100364; Lin, C. Y., Lou, W. S., Chen, J. C., Weng, K. Y., Shih, M. C., Hung, Y. W., Chen, Z. Y., and Wang, M. C. 2020. "Bio-compatibility and Bio-insulation of Implantable Electrode Prosthesis Ameliorated by A-174 Silane Primed Parylene-C Deposited Embedment," Online, Multidisciplinary Digital Publishing Institute Micromachines (Basel, Switzerland) 11(12):1064; Yang, Y., Du, F. S., and Li, Z. C. 2020. "Highly Stretchable, Self-healable, and Adhesive Polyurethane Elastomers Based on Boronic Ester Bonds," American Chemical Society Applied Polymer Materials," (Washington, D.C.) 2(12), pp. 5630-5640; Wendels, S. and Avdrous, L. 2020. "Biobased Polyurethanes for Biomedical Applications," Online, Bioactive Materials (Beijing, China) 6(4):1083-1106; Kim, S. and Liu, S. 2018. "Smart and Biostable Polyurethanes for Long-term Implants," American Chemical Society Biomaterials Science and Engineering (Washington, D.C.) 4(5): 1479-1490). All surfaces of the device in contact with blood, to include the outflow path in FIGS. 3, 4, and 5, are coated with a highly shape-compliant parylene as a moisture barrier.

In comparison, in a highly expandable or distensible valve devised to accommodate growth from early life to late adolescence if not adulthood, the blood outflow channel and cross-furrowed highly stretchable rubbery outer waterproof jacket of implantable highly plasticized silicone elastomer or polyetheretherketone, for example, part number 42 in FIG. 3, are one and the same. However, the two types of vascular valve also share some attributes. In both types, the frontal portion which clutches about the substrate vessel incorporates numerous apertures, or fenestrae, which take up a majority of the surface area of that part.

These openings pass entirely through both the cross-furrowed outer shell and its parylene coated open-cell viscoelastic polyurethane foam lining down to the adventitia so that the foam lining invests, that is, conforms to the shape of, rather than compresses, the tiny vessels, or vasa vasorum, and nervelets, or nervi nervorum, as well as even smaller protective structures, that support the substrate vessel. In some implementations, babies and toddlers, some or all tubular parts of the system, to include vascular valves, bloodlines, druglines, and confluence conduits, are made to grow in step with the patient using the nonallergenic rubbery cross-furrowed highly stretchable sheet stock of silicone rubber, and not applied to living tissue. Furthermore, such implementations can lack apertures.

Where for the adventitia to be entirely closed off would initiate the atherosclerotic degeneration of the substrate vessel with consequent graft failure, the apertures afford sufficient contact of the vasa vasorum and nervi vasorum of the substrate vessel with the surrounding serous fluid. The rapidly adverse consequences of fully enclosing the adventitia is prominent in the literature and is cited in copending continuation-in-part application Ser. No. 19/033,348. In FIG. 3, the triple and double layer furrowed material of the growth-compliant distensible vascular valve for small children is sufficiently elastic that the cross-furrowing in one direction does not significantly interfere with expansion in the other direction at right angles to it.

The lumen of the valve is sized to accommodate perivascular fat, which important for vascular homeostasis, vascular wall physiology, and immune function, is carefully punctured though in alignment with the apertures or fenestrae through the other layers surrounding the substrate vessel (see for example, Simantiris, S., Pappa, Papastamos, C., Korkinikitis, P., Antoniades, C., Tsioufis, C., and Tousoulis, D. 2024. "Perivascular Fat: A Novel Risk Factor for Coronary Artery Disease," Online, [Multidisciplinary Publishing Institute]*Diagnostics* 14(16):1830).

To allow the automatically triggered saturation with a drug such as anti-inflammatory, immune tolerance inducing, or antimicrobial by the implanted disorder response system, in both ordinary vascular valves such as that shown in FIG. 2 and highly distensible vascular valves such as that shown in FIG. 3, except in the foam-free apertures, the foam lining the portion of the vascular valve encircling the substrate vessel in the adventitia is open-cell.

Provided exposure of the adventitia exposed to the serous fluid is sufficient, treatment through the automatic release of ameliorating medication by the automatic response system should be needed seldom if ever. Drug- and bloodlines in a small child are constituted as described above where the pliancy thereof also alleviates problems of strangulation, compression, and kinking. In an adult, if thought necessary, an antikinking line is made of silicone rubber, for example, with side channels running entirely along the line, much as a drainage line used with an internal urinary catheter.

Thin film system sensors for example, signal the master control microprocessor to automatically release medication as necessary. Accordingly, the lesser sum area of the substrate adventitia aside from the apertures in contact with the open-cell foam lining the outer shell rather than serous fluid in a FIG. 2 type vascular valves are wetted with drugs delivered to treat the vasa and nervi vasorum with a steroid or antimicrobial, for example, through drugline 8'. FIG. 2 a longitudinal cross section, additional such druglines can be positioned at various point about the circumference of the valve. The outflow or sidestem portions of both ordinary and highly distensible valves 19 have no part in contact with the substrate vessel and therefore have no need of a foam lining.

Electrical conductors in an adult are provided with a cushioning outer layer of insulation and routed to avoid strangulating or otherwise interfering with tissue along their passage. Those in a pediatric patient are no different but originally placed with their eventual length folded over on themselves to unfold with growth. To be certain that despite lacking a solid polymeric outer jacket as in an ordinary vascular valve, a highly distensible vascular valve will remain leakproof indefinitely, its sidestem, or blood outflow channel 19, is lined with a thick impermeable ply of polyethylene, for example, if necessary, wrinkled.

This is sufficiently plasticized and strongly bonded to the outer layer as to be compliant without posing resistance to the enlargement of the apertures, the layers stretching together responsive to growth (see, for example, Bernal-Chávez, S. A., Alcalá-Alcalá, S., Almarhoon, Z. M., Turgumbayeva, A., Gurer, E. S., De Los Dolores Campos-Echeverria, M., Cortés H., and 4 others 2023. "Novel Ultra-stretchable and Self-healing Crosslinked Poly (ethylene oxide)-Cationic Guar Gum Hydrogel," Online, BioMed Central Journal of Biological Engineering (London, England) 17(1):64; Wang, S., Nie, Y., Zhu, H., Xu, Y., Cao, S., Zhang, J., Li, Y., and 3 others 2022. "Intrinsically Stretchable Electronics with Ultrahigh Deformability to Monitor Dynamically Moving Organs," Online, Science Advances (Washington, D.C.) 8( )13)eab15511; Jing, H., Feng, J., Shi, J., He, L., Guo, P., Guan, S, Fu, H., and Ao, Y. 2021. "Ultra-stretchable, Self-recovering, Self-healing Cationic Guar gum/Poly(stearyl Methacrylate-co-acrylic acid) Hydrogels," Carbohydrate Polymers (London, England) 256:117563; Nguyen, N. T., Milani, A. H, Jennings, J., Adlam, D. J., Freemont, A. J., Hoyland, J. A., and Saunders, B. R. 2019. "Highly Compressive and Stretchable Poly (ethylene Glycol) Based Hydrogels Synthesised Using pH-responsive Nanogels without Free-radical Chemistry," Nanoscale (Cambridge, England) 11(16):7921-7930; Le Floch, P., Meixuanzi, S., Tang, J., Liu, J., and Suo, Z. 2018. "Stretchable Seal," American Chemical Society Applied Materials and Interfaces (Washington, D.C.) 10(32):27333-27343).

Provided with a relatively thick outer shell lining of high density viscoelastic polyurethane foam coated with 200 percent expandable and fully compliant vapor-deposited parylene and apertures to protect the tiny structures about the outer surface of larger vessels, the ordinary vascular valves shown in copending continuation-in-part application Ser. No. 19/033,348 should accommodate growth in patients past the initial period of rapid growth from baby to young adolescent when the rate of growth from older adolescent to adult subsides. For babies and toddlers, however, vascular valves, bloodlines, and druglines with considerably greater distensibility or expandability eliminate, or at the very least forestall, the eventual need for surgical reentry to replace these upon reaching adolescence if not adulthood.

Ordinary vascular valves cannot provide this degree of expandability. FIG. 1 shows the blood flow pattern midway in the process of transferring the donor heart from the circulatory system of the donor into that of the recipient. In FIG. 1, part number 1 is the lumen and part number 2 the outer walls of the substrate arteries and veins respectively; 9 is the bloodline connecting the recipient to the donor cardiac arteries; 9' to the bloodline connecting the recipient to the donor heart cardiac veins; part number 196' denotes the conveyance of blood flow from a single vein, and 230 a confluence conduit which conveys the combined flow of plural vessels carrying oxygenated blood, part number 18 to the blood flow path diversion chutes; 41 to the blood flow paths; and 45 to the cut ends of the arterial and drainage stumps once excised.

FIG. 2 shows a conventional or ordinary vascular valve for use in an older child or adult as described in U.S. Pat. No. 11,759,186 and copending continuation-in-part application Ser. No. 19/033,348. Accommodating of growth according to the thickness of the foam lining the outer shell, such a valve will accommodate growth but not extensively so, meaning not all the way from a baby or toddler to an adolescent or adult. In FIG. 2, part number 1 is the lumen of the substrate vessel, 2 the outer wall of the vessel; 3 the polymeric jacket of the sidestem; 4, the highly expansion-compliant parylene-coated viscoelastic polyurethane foam of a closed-cell layer outside an open-cell layer for separating the substrate vessels from the polymeric parts of the valve which would otherwise injure the small vessels and nerves of the adventitia; and parts number 40, the apertures that allow contact between the fine support structures about the outer surface of the substrate vessel.

Part number 5 points to the outlet end of the sidestem outflow tube where the effluent bloodline is connected; and 6 to the razor-sharp trepan front leading edge of the same part used to draw out a plug for entry of the blood flow diversion chute 18. Part number 8' is a valve drugline inserted into a valve upper accessory channel which gives access to the adventitia of the substate vessel to allow liquid drugs to permeate the open-cell foam; while 8 is a drugline integral to the driver-diversion chute-connecting line; and 10 is the sidestem endcap.

Alternatives, such as double outlet hydraulic valves which gradually adjust the apportionment of outflow from a single fluid delivery line between two outlets are not applicable and contrary to the basic object and advantage of the invention in eliminating the need to transect the substrate vessel. To do so requires that circulation through the vessel be interrupted. In the larger vessels of an organ recipient undergoing a vascular bypass organ, especially a heart transplant, clamping and transection of the corresponding vessels of the donor and recipient to be connected necessitate the use of mechanical circulatory support for the recipient.

The surgery, cardioplegia, and general anesthesia this requires are more highly susceptible to the inducement of desynchronizations and vasospasm as well as other complications. In comparison, the relatively gentle handling of the vessels in a vascular bypass transplant inflicts less trauma and injury, making the operation a realistic prospect for patients who would otherwise have to be declined. Nevertheless, the propensity toward vasospasm is sufficiently pronounced that even a vascular bypass transplant is attended by means for resynchronization where it is less likely to be needed.

Whether monomorbid and controlled by an implanted microcontroller or multimorbid and controlled by a master control microprocessor under hierarchical control pursuant to a prescription-program, the detailed circuitry in an automatic disorder response system is familiar to those skilled in the art, to include electrical electronics, automatic control, and computer engineers.

Other parts shown in FIG. 2 are 11, the valve lock clasp receivers, 13, the left-hand arterial wall, 14, the right-hand arterial wall, 15, a suture eyelet to allow the use of suture to adjust the position of or stabilize the valve, 19, the sidestem blood outflow channel, 27, 30, the valve entry opening and blood outlet ostium obturator, 31, the drugline 8 outlet pore, 32, the diversion chute 18 driver plunger solenoid. 33, the connector of the solenoid plunger (thrust rod, slider, shaft) to accessory channel 8, 34, the solenoid electromagnetic coil or winding, 35 the solenoid compression spring, and 36 the solenoid plunger, 35, 36, and 41, the blood flow directional indicator.

Also in FIG. 2, shown in the upright position, drugline 8' is inserted directly into an opening, a simple accessory channel, in an ordinary or limited growth-accommodating vascular valve. Liquid drugs delivered through this line wet the open-cell foam lining of the valve at the vessel-encircling front of the valve in direct contact with the adventitia to treat the tiny nerves and vessels at the outer surface of the vessel thus reducing any irritation that the valve might otherwise cause.

The sectional view provided by FIG. 2 does not show the other such druglines about the circumference of the valve which together wet the entire foam-covered adventitia. To minimize the number of druglines needed to supply the valve, the line departing the drug reservoir implanted subcutaneously in the pectoral region gives off branches such as 8' and the other points about the valve circumference. The same reservoir-initiated drugline as that providing the branch 8' could also provide 8 which is not a branch but singular; however, the drugs to either destination would often be different.

In nondistensible form, the valves and method are no less suitable for use by a urological, hepatological, or pulmonary surgeon, for example, in an adult, often one elderly, affected by multimorbid disease, often end-stage heart disease, and less able to tolerate the conventional procedure, will then be left to die. As described herein, in a small child, the desirability of removing the valves and replacing these with separate directly pipe-targeted automatic postoperative drug delivery lines which remain under the control of the implanted disorder response system is satisfied by the replacement drugline-securing means shown in FIG. 5. Removal and replacement should be undertaken only when—despite the latitude in rotational angle and level along the substrate vessel, no position can be found that would provide the child complete comfort.

During transfer of the graft heart from the circulatory system of the donor into the circulatory system of the recipient as depicted in FIG. 1, the vascular valves such as shown in FIG. 2 are in the fully blood diversion chute-extended or substrate lumen closed-off position whereby all blood flow is diverted out the sidestem and synthetic bloodline, and as seen in FIG. 1, passed from the donor to the recipient heart in the upper arterial and from the recipient to the donor in the lower venous lines.

Slightly opening the valves reduces the local blood pressure above the tip of the blood diversion chute 18 reducing the shear stress at the local levels of reduced pressure, hence, any damage to the erythrocytes, while it increases the local blood pressure just past the tip where the system controller can coordinate the release of a drug such as an inotrope and/or immunosuppressive through drugline pore 31 in FIG. 2 for better penetration into the intima. If the blood pressure would best be increased, such as to gain better uptake of an inotrope or a drug into the intima because the recipient organ lacked sufficient venous return pressure to propel the blood to the donor organ at the pressure desired, partial retraction of the diversion chute to divert a small proportion of blood past it and into the recipient vessel can be used to adjust the pressure.

Removal of the valves used to perform a vascular bypass heart transplant with their replacement with independent drug delivery lines such as that shown for an adult in FIG. 4 and for a small pediatric patient in FIG. 5 is primarily justified when to retain these causes the patient discomfort. There may, however, be justification in allowing one or more of the valves to remain in place postoperatively. One use thus is to allow an extracorporeal or remote adjustment in blood pressure without the need for reentry which can cause long term pain.

Retention of the valves in place following a vascular bypass heart or other solid organ transplant offers certain advantages. Remote increase in the local blood pressure along a vessel without reentry and or sensation can be used to temporarily modulate the local uptake of a drug dissolved or dispersed in the blood, and combined with direct pipe-targeting, increased local blood pressure can be used to further increase the uptake of a drug dispersed in the blood.

In conjunction with other equipment in the clinic such as magnetic resonance imaging, micro- and/or nanoparticles dispersed in the blood can also serve a warming function. Macrophages have also been used for the " . . . targeted transport of drugs: they efficiently take up a broad spectrum of nanoparticles (NPs) and, by sensing cytokine gradients, they are attracted to the sites of infection and inflammation" (Desai, O., Kumar, S., Köster, M., Ullah, S., Sarker, S., Hagemann, V., Habib, M., and 6 others 2025. "Macrophages Co-loaded with Drug-associated and Superparamagnetic Nanoparticles for Triggered Drug Release by Alternating Magnetic Fields," Online, *Drug Delivery and Translational Research* (New York. New York) 15(8):2779-2793).

Moreover, the effect can be considerably increased by bonding the medicinal molecule to a superparamagnetic iron oxide micro- or nanoparticle-carrier, that is, a magnetically susceptible or magnetized micro- or nanoparticle-carrier where a magnetized perivascular collar had been positioned in advance of the organ transplant—a medicinal ion trap (see, for example, Alfei, S. and Zuccari, G. 2025. "Last Fifteen Years of Nanotechnology Application with Our Contribute," [Multidisciplinary Digital Publishing Institute] *Nanomaterials* (Basel, Switzerland) 15(4):265; Vukaditiović, A., Ognjanović, M. Mijović, M., Warren, B., Erić, S., and Prijović, Ž. 2025. "Lignin-based Nanocarrier for Simultaneous Delivery of $^{131}$I and SN-38 in the Combined Treatment of Solid Tumors by a Nanobrachytherapy Approach," Online, [Multidisciplinary Digital Publishing Institute]*Pharmaceuticals* (Basel, Switzerland) 18(2):177; Saba, I, Batoo, K. M., Wani, K., Verma, R., and Hameed, S. 2024. "Exploration of Metal-doped Iron Oxide Nanoparticles as an Antimicrobial Agent: A Comprehensive Review," Online, *Cureus* (Palo Alto, California) 16(9): e69556; Salehirozveh, M., Dehghani, P., and Mijakovic, I. 2024. "Synthesis, Functionalization, and Biomedical Applications of Iron oxide Nanoparticles (IONPs)," Online, Multidisciplinary Digital Publishing Institute]*Journal of Functional Biomaterials* (Basel, Switzerland) 15(11):340; Zhang, T. G. and Miao, C. Y. 2024. "Iron oxide nanoparticles as Promising Antibacterial Agents of New Generation," Online, [Multidisciplinary Digital Publishing Institute]*Nanomaterials* (Basel, Switzerland) 14(15):1311; Vangijzegem, T., Lecomte, V., Ternad, I., Van Leuven, L., Muller, R. N., Stanicki, D., and Laurent, S. 2023. "Superparamagnetic Iron Oxide Nanoparticles (SPION): From Fundamentals to State-of-the-art Innovative Applications for Cancer Therapy," Online, *Pharmaceutics* (Basel, Switzerland) 15(1):236; Dadfar, S. M., Camozzi, D., Darguzyte, M., Roenmhild, K., Varvarà, P., Metselaar, J., Banala, S., and 11 others 2020. "Size-isolation of Superparamagnetic Iron Oxide Nanoparticles Improves MRI [magnetic resonance imaging], MPI [magnetic particle imaging], and Hyperthermia Performance," Online, (BioMed Central) *Journal of Nanobiotechnology* (London, England) 18(1):22; Duliiska-Litewka, I., Łazarczyk, A., Halubiec, P., Szafrański, O., Karnas, K., and Karewicz, A. 2019. "Superparamagnetic Iron Oxide Nanoparticles—Current and Prospective Medical Applications," Online, [Multidisciplinary Digital Publishing Institute]*Materials* (Basel, Switzerland) 12(4):617; Alexiou, C. 2013. "Nanornedizin. Innovative anwendungen in dermedizin [in German—Nanomedicine. Innovative Applications in Medicine]. HNO [Hals-Nasen-und Ohrenärzte]61(3):197-201).

One application of a medicinal ion trap in a pre-end stage heart is the topical or direct contact application of a statin with the atheromatous intima. The topical efficacy of statins is now established (see, for example, Bittencourt, M. S. and Cerci, R. J. 2015. "Statin Effects on Atherosclerotic Plaques: Regression or Healing?," Online, BioMed Central *Medicine* (London, England) 13:260; Hattori, K., Ozaki, Y., Ismail, T. F., Okumura, M., Naruse, H., Kan, S., Ishikawa, M., and 8 others 2012. "Impact of Statin Therapy on Plaque Characteristics as Assessed by Serial OCT [optical coherence tomography], Grayscale and Integrated Backscatter-IVUS [intravascular ultrasound]," Online, *Journal of the American College of Cardiology Cardiovascular Imaging* (New York. New York) 5(2):169-177; the intravascular topical efficacy of statins is reviewed in greater detail in copending continuation-in-part application Ser. No. 19/033,348, entitled Vascular Valves and Servovalves—and Prosthetic Disorder Response systems).

The fact that individual and multiple valves and perivascular collars can be positioned at any level and rotational angle makes drug targeting thus versatile. Using a state of the art permanent magnet, currently one incorporating neodymium iron boron, the degree of attraction toward a magnetized perivascular collar can be set at a preferred value, or by using an electromagnetic collar, made variable. Magnetized perivascular vascular collars are described in U.S. Pat. No. 11,389,171.

As indicated, independent drug delivery lines, or druglines, are shown in FIGS. 4 and 5. These can be used to affix a drugline to a substrate vessel in implanting an automatic prosthetic disorder response system to treat any chronic serious disorder or to allow removal of a vascular valve used to perform a vascular bypass organ transplant if such had caused the patient discomfort. To prevent the reflux of blood into valves, druglines, independent druglines, and the terminals of confluence conduits all druglines have a spring return one-way valve at their terminal end, shown as part number 9 in FIG. 5, and this is no less so as to independent druglines for placement when the vascular valves used to perform the transplant are to be removed.

Independent druglines are not only used to treat any chronic serious condition with an implanted disorder response system but can replace the druglines in vascular valves used to perform an organ transplant when removal of the valves is desired. This is because drugline 8' supports the external wall of the substrate vessel, whereas drugline 8 supports the internal wall. Drugline 8 would typically be used to release a topically effective antithrombotic drug such as a heparin, or an antimicrobial to ward off infection, or an anti-atherosclerotic statin and/or lecithin, for example. Amenable to saturation by liquid drugs delivered to wet the adventitia through drugline 8', open-cell layer of foam 4 is bonded to the internal surface of the hard outer shell 3.

Rather than directed to the outer surface of the substrate vessel, drugline 8 delivers liquid drugs through the underside aperture 31 of blood flow diversion chute 18 so that as blood flow diversion chute 18 is withdrawn, more of the drug flows past it. The introduction into the bloodstream at any point in FIG. 1 will eventually be distributed throughout the circulatory system, so that such a drugline could be attached at any point in FIG. 1.

As shown in FIG. 4, upon completion of a vascular bypass organ transplantation, if the valves are to be removed, pipe-targeted drug delivery for continued medicinal support of the substrate vessel intima can continue through a non-jacketing side-entry connector. As shown in FIG. 5, continued medicinal support of the adventitia can be accomplished through a drugline connected to a band encircling the substrate vessel where the 200 percent expandable parylene vapor-deposited or sputter-coated high-density open-cell viscoelastic polyurethane foam lining the band will become saturated with the medication.

A drugline connected directly to the outer surface of a vessel or to the fibrosa of any other organ or tissue is attached to the substrate surface by a nonjacketing side-entry connector as shown in U.S. Pat. No. 11,013,858, which also describes such connectors wired to deliver electrostimulatory discharge pulses at any rate in any pattern through the anchoring needles of the connector. Hollow anchoring needles can be connected to druglines to inject drugs as well as to deliver electrostimulatory discharge pulses, and when appropriate, and as described, can carry a temporary disintegrable radiation shield that will afford sufficient protection for the delivery of moderate dose radioisotopes or radionuclides with a half-life shorter than that of the shielding. Solid nichrome or tungsten anchoring needles can heat the surrounding tissue, while to activate a prodrug, for example, hollow anchoring needles can warm the injectant.

FIG. 3 shows a highly distensible vascular valve for connecting the corresponding vessels in a vascular bypass organ transplant in an infant or young patient. In FIG. 3, part number 1 is the lumen of the substrate vessel, 2, its wall, 5, the opening for insertion of the blood outflow line, 8, the lower drug delivery line, or drugline, 8', the upper drugline, 13, the left-hand and 14, the right-hand intima of the substrate vessel, 15, a suture loop to pass through suture in order to adjust the position of the valve or stabilize it, if necessary, by suturing to neighboring tissue. Part number 17 is a parylene-coated rivet to lock the bottom of the driver enclosure to the polytetrafluoroethylene-coated silicone rubber floor thereby to stabilize the driving solenoid or servomotor enclosure in position as the non-driver portions of the valve expand in diameter and to either side.

In FIG. 3, the callout at the upper right indicates suitable layers in the frontal portion of a highly distensible vascular valve encircling the substrate vessel. From right to left, these are: 1. The highly elastic and furrowed outer layer of a silicone rubber or another polymeric material exhibiting similar properties, 2. To invest rather than compress the and nervi vasorum, a viscoelastic polyurethane form layer lining fully compliant with the rubbery stretchable layer at the external surface which it lines, and 3. To prevent the foam from chemical breakdown, an internal coating of elastic parylene lining the internal surface of the foam in contact with the external surface of the substrate vessel.

The callout at the upper left indicates suitable layers in the blood outflow sidestem portion of a highly distensible vascular valve need not protect a vessel but must neither rupture nor absorb moisture. From left to right, these are: 1. The highly elastic and furrowed outer layer of a silicone rubber or another polymeric material exhibiting similar properties continuous with the same layer about the outer surface of the vessel encircling forward portion of the valve, 2. The compliant lining of the outer highly expandable layer comprising a polyethylene-based hydrogel, for example, and 3. An optional coating of parylene to isolate the second layer from the passing blood.

The callout at the bottom left indicates the outer rubbery furrowed layer as continuous with that fully encircling the valve to also enclose the driver compartment which is isolated both from the substrate vessel and the flow of blood. Other layers internal to that outermost are nonadherent to it and provided to allow that outermost to slide over the relatively hard polymeric or metallic enclosure of the driver compartment without risking rupture of the outer layer, a highly elastic low or no resilience polytetrafluoroethylene suitable.

Part number 16 the frontal portion of the valve encircling the substrate vessel, 19, the sidestem blood outflow channel behind the portion of the valve that encircles the substrate vessel, 40, an aperture through the outer rubbery furrowed covering of the valve 41, a blood flow direction indicator, 42, the outer rubbery furrowed covering of the valve, and 100, the valve driver compartment ceiling which separates the blood passing through the sidestem, or blood outflow channel, 19 from the valve driver compartment 101.

In FIG. 3A, upper sidestem or blood outflow portion 19 and lower driver compartment 101 are each consigned to mutually isolated chambers which are inseparably heat laminated together at their interface. A slideway is provided for the movement of blood flow diverter 18 through an integrally molded channel in the bottom of compartment 101.

As shown in FIG. 3, part number 1 is the lumen and parts number 2 the side walls of a single vessel in a highly expandable pediatric vascular bypass solenoid-driven valve or servomotor-driven servovalve. All parts of the outermost layer comprise a stretchable outer cross-furrowed outer jacket consisting of a 2.0-millimeter-thick high tensile strength nonallergenic rubbery sheet stock. The outer jacket can consist of an implantable highly plasticized silicone elastomer or polyetheretherketone, for example, with longitudinal and transverse or cross-furrows or ruts that render it considerably expandable or stretchable in both caliber or bore and length without significant restorative force.

While the outermost layer enclosing the upper frontal and outflow portions of the valve is a unit, in effect a balloon, the layers lining that outermost differ between the frontal portion 16 where the substrate vessel must be protected and the sidestem or blood outflow portion 19 where only rupture prevention is required. Driver compartment 101 is enclosed in a second outer enclosure of like composition as outflow portion 19 not requiring apertures and foam lining and bonded to the underside of blood outflow or sidestem portion 19. Accordingly, in the frontal portion 16, the outer jacket has bonded to it an inner 2.0 millimeter lining of 200 percent expandable parylene vapor-deposited or sputter-coated high-density open-cell viscoelastic polyurethane foam incorporating apertures or fenestrae as addressed above.

As indicated, to withstand chemical breakdown despite being in direct contact with the passing blood, the open cell viscoelastic polyurethane foam is coated with a highly compliant parylene. To prevent the foam from restricting the size of the through and through perforations to the substrate adventitia as the outer layer expands, the foam of the lining must be formulated so that it expands in step with the expandable outer layer, which will depend at least in part upon the incorporation of sufficient plasticizer. In a small child, such expandable material is used in every component of the implanted system.

The sidestem or blood outflow portion 19 and driver compartment 101 are lined with the highly stretchable and tensile strength polyethylene layer, usually a hydrogel, specified above. The upper outflow and lower driver compartments are bonded together to present the outer appearance of a unit. Sharp corners and edges of the distensible valve soft outer shell lacking and protrusion into neighboring structures avoidable by adjusting the position along and radial angle of the valve in relation to the substrate vessel, even when placed in an infant, the 0.8 centimeter addition to the outer diameter of the great muscular and elastic vessels should not result in encroachment upon neighboring structures by the valves.

In general, the preferred thickness of the linings is that least reduced to avoid complications. Clinical judgement may also opt for an alternative jacketing material described in copending continuation-in-part application Ser. No. 19/033,348, paragraph 2b(2)(f), entitled Expandable Structure to Accommodate Growth and Self-adjust in Size in Vascular Segment Prostheses, Lines, and Confluence Conduits Placed in Children. Both types of material placed about a substrate vessel expand in caliber or bore responsive to the pressure and volume of blood passed and in length together in step as dictated by the increase in length of the substrate vessel to which the material is attached.

At the same time, the material of the sidestem also expands in caliber in response to the increase in blood pressure and volume associated with growth and the pull exerted by the vessels to which the sidestem is indirectly attached. The part of the highly expandable valve that clutches about the substrate vessel made of the cross-furrowed silicone or polyetheretherketone sheet stock material is profusely perforated and of the high-density viscoelastic polyurethane foam lining, one longitudinal furrow serves as the hinge between the semicylindrical sides. To protect the vasa and nervi vasorum of the substrate vessel, this part of the valve incorporates perforations which profuse and extensive as practicable, pass entirely through both the sheet stock and foam lining to the surface of the substrate vessel.

As fully documented in U.S. Pat. No. 11,759,186, entitled Ductus Side-entry Jackets and Prosthetic Disorder Response Systems as well as in pending continuation-in-part application to parent application Ser. No. 16/873,914, namely Ser. No. 19/033,348, this feature has been proven to avoid the deterioration of the vasa and nervi vasorum in the induction of atherosclerotic degeneration. Made of synthetic materials in both ordinary and highly expandable vascular valves, valve sidestem, part number 19 in the drawing figures, does not encircle and need not accommodate a living vessel. It can therefore consist of cross-furrowed silicone or polyetheretherketone sheet stock, for example, with neither perforations nor a conformant foam lining.

To encircle the substrate vessel, the longitudinal furrow at the front center of the valve serves as the side-to-side junction between the semicylindrical sides. The sides lock together by snap-in undercut insertion to provide a moisture-tight joint. The sidestem is solid all around and does not require a hinge. A crucial requirement for great duration in the face of ongoing expansion without the need for reentry and replacement is that the seams where the half-cylinders of the vessel-encircling portion of the valve as well as all other points along the valve be leakproof absolutely and forever.

To this end, the edges of either side fit flush together along their entire lengths, one side additionally providing an overlapping longitudinally running lip enclosing the opposite edge, with the covert edge provided with a longitudinal elevation that firmly snaps into a complementary groove in the overlapping lip. To accommodate growth without a loss in the adequacy of pulsatile circulatory function, all parts of the vascular valves and not just the outer layer must expand together.

To assure a leak-proof seal inside of the valve, the flow diversion chute, or tongue, as in ordinary vascular valves, is thinned out or feathered in thickness toward the edges but here, sufficiently so to unfold radially outward in step with growth and with sufficient restorative force to remain flush to the internal surface, or intima, of the substrate vessel. At the same time, the throw of the driver if a linear plunger solenoid is set for the adult distance greater than that of the space afforded at the time of placement, wherewith to prevent a startling internal sensation of snapping, plunger solenoids must be highly damped as well as nonsparking.

Otherwise, whether solenoid or servovalve, the driver within driver compartment 101 would appear no differently than as shown in FIG. 2. A thin-film stretch or pressure sensor positioned almost anywhere in the body and integrable in the either drugline mounting shown in FIGS. 4 and 5 can report the degree of growth to the disorder automatic response system master control microprocessor. Proportionally driven according to the increase in strain due to stretching or pressure since implantation as reported by the sensor or sensors to the master control microprocessor, the distance of extension of diversion chute 18 into the lumen of the substrate vessel 1 is scaled to correspond to the contemporary size of the patient. FIG. 4 shows a nondistensible nonjacketing side-entry connector as described in detail in U.S. Pat. No. 11,013,858, entitled Nonjacketing Side-entry Connectors and Prosthetic Disorder Response Systems. Such a connector is for use to connect a line directly to the surface of an organ, or as shown here, a great vessel. Attachment to a substrate vessel as depicted in FIGS. 4 and 5 can be used (e.g., in adults) to replace the drugline of a vascular valve removed along with the defective native organ at the conclusion of a vascular bypass organ transplant to allow the continued automatic delivery of drugs by the implanted disorder response system once the vascular valves had best been removed.

Replacement of the valve with the independent drug delivery line, or drugline, is by withdrawing the valve, quickly placing the thumb over the ostium, then inserting the distal end of the drugline through the ostium. Various means for inseparably attaching the drugline to the substrate vessel are possible, that shown in FIG. 4 using anchoring needles which immediately after withdrawal of the thumb and pressing the nonjacketing side-entry connector down to sustain containment of the blood, are rotated around one at a time to undercut the vessel surface short of the intima.

In a nonjacketing side-entry connector as shown in FIG. 4 for an adult, the top plate is made of a solid polymer. For a small child, however, the top plate of the connector shown in FIG. 4, must allow the anchoring needles to slide outwards with growth, and must therefore expand in step with the rate of increasing separation between the anchoring needles. The top plate can also serve to report the degree of growth to the automatic implanted system master control microprocessor.

To this end, it is made, for example, of a highly elastic low or no resilience polytetrafluoroethylene (see, for example, Yu, R., Wang, C., Du, X., Bai, X., Tong, Y., Chen, H., Sun, X., and 5 others 2024. "In-situ Forming Ultra-mechanically Sensitive Materials for High-sensitivity Stretchable Fiber Strain Sensors," Online, National Science Review (Oxford, England) 11(6):nwae158; Liu, S., Xu, L., Yu, J., Si, Y., and Ding, B. 2023. "Amphiphobic, Thermostable, and Stretchable PTFE Nanofibrous Membranes with Breathable and Chemical-resistant Performances for Protective Applications," [American Chemical Society] Applied Polymer Materials (Washington, D.C.) 5(2):1464-1473; Li, M., Chen, L., Li, Y., Dai, X., Jin, Z., Zhang, Y. Feng, W., and 3 others 2022. "Superstretchable Yet Stiff, Fatigue-resistant Ligament-like Elastomers," Online, Nature Communications (London, England) 13(1):2279; Yoon, S., Yong, J. K., Lee, Y. R., Lee, N.-E., Won, Y., Gandla, S., Kim, S., and Han-Ki, K 2021. "Highly Stretchable Metal-Polymer Hybrid Conductors for Wearable and Self-cleaning Sensors," Online, Nature Portfolio Asia Materials 13(4); Jiang, Y., Liu, Z., Wang, C., and Chen, X. 2019. "Heterogeneous Strain Distribution of Elastomer Substrates to Enhance the Sensitivity of Stretchable Strain Sensors," [American Chemical Society] Accounts of Chemical Research (Washington, D.C.) 52(1):82-90).

Also in FIG. 4, to protect the vasa and nervi vasorum of a larger or great vessel, the lower layer at the base of the connector is a highly compliant open-cell parylene-coated viscoelastic polyurethane foam as described above, while the upper layer is somewhat greater in density to prevent rocking of the drugline away from vertical if nudged by contact with neighboring tissue. Both layers of foam at the base of the connector of the connector incorporate elongated apertures, which patent entirely through from the connector surface to the external surface of the vessel, allow serous fluid to come into contact with the adventitia as essential to prevent atheromatous degeneration. The length of the connector is gauged to allow extension for the growth to ensue. During growth, the anchoring needles slide along their respective sides, or wings, of the connector through polytetrafluoroethylene-coated channels, or raceways, enclosing the anchors at their proximal ends.

In FIG. 5, the millimetric width of the smaller vessel-encircling collar in a baby or toddler with locking clasp, much as in a bracelet, is too slight to prompt the atheromatous degeneration that follows enclosure of a greater area of adventitia as occurs with a larger vessel. The sectional view does not show parts of the collar such as the clasp lock outside of the plane of the section. In this circumstance, a surround of a highly stretchable polymer such as silicone rubber or elastomeric polyetheretherketone with a coating of stretchable parylene over its internal surface is adequate.

FIG. 5 shows a cross-section through a connector for an independent drugline used to replace a drug delivery line, or drugline to a smaller vessel, which had been incorporated into a vascular valve removed from a smaller vessel upon completion of a vascular bypass organ transplant (e.g., in a baby or toddler). As indicated, a small vessel will necessitate fewer if any apertures or fenestrae to protect what in larger vessels that will remain small through adulthood does not require vasa vasorum and nervi nervorum. Accordingly, the treatment and material of the perivascular collar encircling the vessel much as a bracelet with locking clasp, to include the furrowed highly stretchable jacket to accommodate growth, is simpler than that specified for the vessel-encircling frontal portion of the valve shown as part number 16 in FIG. 3 for a large vessel.

What is claimed is:

1. A perivascular valve configured for encircling a blood vessel of a pediatric patient, the perivascular valve comprising:

a valve body and, the valve body defining an integral tubular blood outlet passageway sidestem extending perpendicularly from said valve body, the integral tubular blood outlet passageway sidestem configured to be continuous with a lumen of the blood vessel, wherein the perivascular valve is selectively positional, such that the perivascular valve with the integral tubular blood outlet passageway sidestem can be positioned at any anatomically available level and rotational angle along the blood vessel, wherein the integral tubular blood outlet passageway sidestem comprises a driven polymeric tongue having an upturned front end configured as a blood outflow diversion chute which is extendable a controllable distance into the lumen of the blood vessel so as to draw off a controllable volume of blood between zero and one hundred percent into said integral tubular blood outlet passageway sidestem for discharge through the integral tubular blood outlet passageway sidestem, wherein said driven polymeric tongue further comprises an outlet pore on an underside of the driven polymeric tongue, the outlet pore being in fluid communication with a drugline configured to deliver a liquid drug into the lumen of the blood vessel downstream from the blood outflow diversion chute, wherein the valve body comprises a stretchable material comprising expandable furrows to allow radial expansion of the perivascular valve so as to accommodate growth in the pediatric patient.

2. The perivascular valve according to claim 1, wherein said stretchable material is made of a chemically inert and elastic polymer.

3. The perivascular valve according to claim 2, wherein the chemically inert and elastic polymer is silicone rubber.

4. The perivascular valve according to claim 1, wherein said stretchable material is made of a plasticized and chemically inert polymer.

5. The perivascular valve according to claim 4, wherein the plasticized and chemically inert polymers is polyetheretherketone.

6. The perivascular valve according to claim 1, wherein the driven polymeric tongue has a feathered surround area which extends radially outward as the perivascular valve enlarges so as to be configured to remain flush against anterior and lateral interior walls of the blood vessel throughout growth of the pediatric patient.

7. The perivascular valve according to claim 1, wherein said driven polymeric tongues is driven in extension and retraction under continuously variable control by a servomotor that is operatively connected to the perivascular valve.

8. The perivascular valve according to claim 1, wherein said driven polymeric tongues is directly driven in extension and retraction between zero and one hundred percent discharge is controlled by a plunger solenoid.

* * * * *